United States Patent [19]

Eglington

[11] 4,413,000
[45] Nov. 1, 1983

[54] β-LACTAM ANTIBIOTICS, THEIR PREPARATION AND USE

[75] Inventor: Alfred J. Eglington, Betchworth, England

[73] Assignee: Beecham Group Limited, England

[21] Appl. No.: 281,553

[22] Filed: Jul. 8, 1981

[30] Foreign Application Priority Data

Jul. 11, 1980 [GB] United Kingdom ............... 8022830

[51] Int. Cl.³ .................... C07D 403/14; A61K 31/41
[52] U.S. Cl. ............................ 424/269; 260/245.2 T; 424/274; 424/114
[58] Field of Search ................. 260/245.2 T; 424/274, 424/269

[56] References Cited

U.S. PATENT DOCUMENTS 4,347,368  8/1982  Christensen et al. ........ 260/245.2 T

FOREIGN PATENT DOCUMENTS 40408  11/1981  European Pat. Off. ..... 260/245.2 T

Primary Examiner—Mary C. Lee
Attorney, Agent, or Firm—Jacobs & Jacobs

[57] ABSTRACT

The present invention provides the compounds of the formula (II):

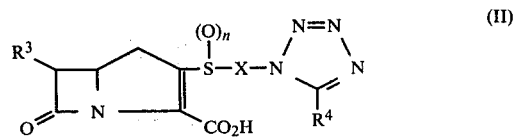

and salts and esters thereof wherein $R^3$ is a hydrogen atom or is an organic bonded via a carbon atom to the carbapenem ring, n is zero or one, X is a saturated or unsaturated hydrocarbon radical optionally substituted by bromo or chloro, and $R^4$ is a $C_{1-6}$ alkyl, $C_{2-6}$ alkenyl, $C_{1-10}$ aralkyl or aryl group, any of such groups $R^4$ being optionally substituted. These compounds are useful as antibacterial agents.

33 Claims, No Drawings

β-LACTAM ANTIBIOTICS, THEIR PREPARATION AND USE

This invention relates to novel antibiotics and to processes for their preparation.

Our co-pending European Patent Application Publication Nos. 0002564, 0005348, 0005349, 007152, 0003740, 0008888, 0008497 and 0007753 describe compounds of the general formula (I):

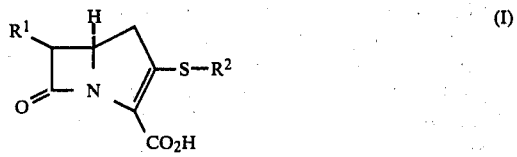

wherein $R^1$ and $R^2$ may independently be selected from a variety of organic groups.

It has now been found that certain of these compounds and related compounds can be converted into novel β-lactam antibiotics which possess desirable antibacterial properties.

Accordingly the present invention provides the compounds of the formula (II):

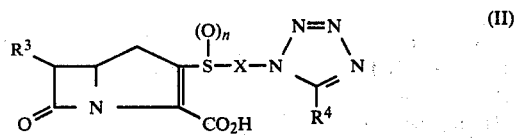

and salts and esters thereof wherein $R^3$ is a hydrogen atom or is organic group bonded via a carbon atom to the carbapenem ring, n is zero or one, X is a saturated or unsaturated hydrocarbon radical optionally substituted by bromo or chloro, and $R^4$ is a $C_{1-6}$ alkyl, $C_{2-6}$ alkenyl, $C_{1-10}$ aralkyl or aryl group, any of such groups $R^4$ being optionally substituted.

When the group $R^3$ represents an organic group, it may be selected from $C_{1-10}$ alkyl, $C_{2-10}$ alkenyl, $C_{2-10}$ alkynyl, $C_{3-7}$ cycloalkyl ($C_{1-6}$) alkyl, $C_{3-7}$ cycloalkyl, aryl, aryl ($C_{1-6}$) alkyl, heterocyclyl, heterocyclyl ($C_{1-6}$) alkyl, heteroaryl, heteroaryl ($C_{1-6}$) alkyl, $C_{1-6}$ alkanoyl, aryl ($C_{1-6}$) alkanoyl, arylcarbonyl and heteroarylcarbonyl, any of the above groups being optionally substituted. Suitably the hetero atom or hetero atoms in the above named heteroaryl and/or heterocyclyl moieties are selected from 1 to 4 oxygen, nitrogen or sulphur atoms. Suitable optional substituents include $C_{1-6}$ alkyl, amino, $C_{1-6}$ alkanoylamino, mono, di- and tri-($C_{1-6}$) alkylamino, hydroxy, $C_{1-6}$ alkoxy, mercapto, $C_{1-6}$ alkylthio, heteroarylthio, arylthio, sulphamoyl, carbamoyl, amidino, guanidino, nitro, chloro, bromo, fluoro, carboxy and salts and esters thereof, $C_{1-6}$ alkanoyloxy, arylcarbonyl and heteroarylcarbonyl.

Suitably $R^3$ is a hydrogen atom or a group of the sub-formula (i):

$$CR^5R^6R^7 \qquad (i)$$

wherein $R^5$ is a hydrogen atom or sulphonate-oxy or salt or ester thereof, hydroxy, $C_{1-4}$ alkoxy, $OCOR^8$ or $OCO_2R^8$ group wherein $R^8$ is a $C_{1-4}$ alkyl, phenyl, or optionally substituted benzyl group; $R^6$ is a hydrogen atom or $C_{1-4}$ alkyl group; and $R^7$ is a hydrogen atom or $C_{1-4}$ alkyl group:

Suitably X is $C_{1-6}$ alkanediyl, $C_{2-6}$ alkenediyl optionally substituted by bromo or chloro, or $C_{3-8}$ cycloalkanediyl: wherein the suffix diyl indicates a divalent radical.

Suitably n is zero. Suitably n is one.

Suitably X is $C_{1-6}$ alkanediyl, more suitably $C_{2-6}$ alkanediyl and preferably —$CH_2$—$CH_2$—. Suitably also X is $C_{2-6}$ alkenediyl optionally substituted by bromo or chloro, more suitably X is —C(Z)=CH— wherein Z is hydrogen, chloro or bromo, favourably Z is hydrogen. Alternatively X is $C_{3-8}$ cycloalkanediyl for example cyclobutanediyl such as cyclobutanedi-1,3-yl, and cyclopentanediyl such as cyclopentanedi-1,3-yl.

Suitable substituents for when $R^8$ is optionally substituted benzyl include fluoro, chloro, bromo, $C_{1-3}$ alkoxy, $C_{1-3}$ alkyl and nitro.

The major utility of the compounds of the formula (II) and salts and esters thereof, is as pharmaceuticals and accordingly the salts and esters of the compounds of the formula (II) are preferably pharmaceutically acceptable; the esters for example may be in-vivo hydrolysable. The compounds of this invention both pharmaceutically acceptable and non-pharmaceutically acceptable may be used as intermediates and also as antibacterial agents in non-pharmaceutical usage such as disinfectant or paint additive.

In one preferred aspect the present invention provides the compounds of the formula (III):

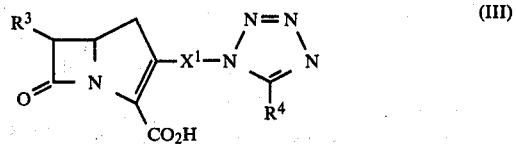

and pharmaceutically acceptable salts and in-vivo hydrolysable esters thereof wherein:

(A) $R^3$ is a hydrogen atom or is a group of the sub-formula (a):

$$CR^5R^6R^7 \qquad (a)$$

wherein $R^5$ is a hydrogen atom or a hydroxy, $C_{1-4}$ alkoxy, $OCOR^8$ or $OCO_2R^8$ group wherein $R^8$ is a $C_{1-4}$ alkyl, phenyl, benzyl, fluorobenzyl, chlorobenzyl, bromobenzyl, $C_{1-3}$ alkoxybenzyl or nitrobenzyl group; $R^6$ is a hydrogen atom or $C_{1-4}$ alkyl group; $R^7$ is a hydrogen atom or $C_{1-4}$ alkyl group; $X^1$ is a group of the sub-formula (b) or (c):

$$-S(O)_n-C_{2-6}- \qquad (b)$$

$$-S-CR^9=CR^{10}- \qquad (c)$$

wherein n is zero or 1; $R^9$ is a hydrogen atom or $C_{1-4}$ alkyl group; $R^{10}$ is a hydrogen atom or $C_{1-4}$ alkyl group; and $R^4$ is a $C_{1-6}$ alkyl, $C_{2-6}$ alkenyl, $C_{1-10}$ aralkyl or aryl group, any of such groups $R^4$ being optionally substituted: or (B) $R^3$ is a $CH_3CH(OH)$-group, $R^4$ is a methyl group, and $X^1$ is a group of the sub-formula (d) or (e):

$$-S(O)-CH=CH- \qquad (d)$$

$$-S-C(Y)=CH- \qquad (e)$$

wherein Y is a bromine or chlorine atom:

(C) $R^3$ is a $CH_3CH(OSO_3H)$-group or methyl or ethyl ester thereof; $R^4$ is a methyl group; and $X^1$ is a group of the sub-formula (f) or (g):

$$-S(O)_n-CH_2-CH_2- \quad (f)$$

$$-S(O)_n-C(Z)=CH- \quad (g)$$

wherein n is zero or 1; and Z is a hydrogen, chlorine or bromine atom: or (D) $R^3$ is a $CH_3CH(OSO_3H)$-group of methyl or ethyl ester thereof; $R^4$ is a $C_{1-6}$ alkyl, $C_{2-6}$ alkenyl, $C_{1-10}$ aralkyl or aryl group, any of such $R^4$ groups being optionally substituted; and $X^1$ is a group $-S-CH_2-CH_2-$: or (E) $R^3$ is a $CH_3CH(OSO_3H)$-group or a methyl or ethyl ester thereof; $R^4$ is an ethyl group; and $X^1$ is a group $-S-CH=CH-$: or (F) $R^3$ is a $CH_3CH(SR^o)$-group wherein $R^o$ is a $C_{1-6}$ alkyl, $C_{2-6}$ alkenyl, $C_{1-10}$ aralkyl, or aryl group; $R^4$ is a methyl group; and $X^1$ is a group $-S-CH_2CH_2-$ or a group of the sub-formula (h):

$$-S(O)_n-CH=CH- \quad (h)$$

wherein n is zero or 1.

In one aspect when $R^3$ is a $CH_3CH(OSO_3H)$-group or methyl or ethyl ester thereof the C-5 and C-6 protons are cis.

Suitably $R^4$ is a $C_{1-6}$ alkyl, $C_{2-6}$ alkenyl, $C_{1-10}$ aralkyl or aryl group, any of such groups being optionally substituted by one or more groups or atoms selected from hydroxy, bromine, chlorine, fluorine, carboxylic acid or salt or ester thereof, azido, tetrazolyl, alkanoyl, alkanoyloxy, aroyloxy, aroyl, aralkanoyloxy, aroxy, amino, protected amino or nitro. For example when $R^4$ is an optionally substituted $C_{1-6}$ alkyl group apt groups include methyl, ethyl, propyl, butyl, pentyl, hexyl, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benzyloxycarbonylethyl, methoxycarbonylmethyl, methoxycarbonylethyl, fluoromethyl and fluoroethyl. When $R^4$ is an optionally substituted $C_{2-6}$ alkenyl group apt groups include propenyl, butenyl, cyclopentenyl and cyclohexenyl. Suitably $R^4$ is an optionally substituted $C_{1-10}$ aralkyl group, for example benzyl, phenethyl, thienylmethyl, furylmethyl, α-hydroxybenzyl, α-carboxybenzyl and salts and esters thereof, α-azidobenzyl, α-tetrazolylbenzyl, α-aminobenzyl, p-hydroxybenzyl, α-amino(p-hydroxy)benzyl and α-carboxy(p-hydroxy)benzyl and salts and esters thereof. Suitably $R^4$ is an aryl group, for example phenyl, furyl, thienyl, hydroxyphenyl, naphthyl, methoxyphenyl, chlorophenyl and methoxycarbonylphenyl.

Most suitably $R^4$ is a $C_{1-6}$ alkyl group for example a methyl, ethyl, propyl or butyl group, of these a preferred value for $R^4$ is methyl as the necessary starting-materials tend to be more readily available.

Suitably $R^3$ is a hydrogen atom or is a group of the sub-formula (a) as hereinbefore defined.

More suitably $R^3$ is a group of the sub-formula (j):

$$CH_3-CH- \quad (j)$$
$$\phantom{CH_3-}|$$
$$\phantom{CH_3-}R^{11}$$

wherein $R^{11}$ is a hydrogen atom or a hydroxy, $C_{1-4}$ alkoxy, $O.CO.R^8$, $OCO_2R^8$ or $SR^8$ group or $-SO_3H$ group or methyl or ethyl ester thereof, wherein $R^8$ is as hereinbefore defined. The necessary starting-materials for compounds of the formula (II) with such values of $R^3$ are readily available from natural products or are readily synthesised from natural products.

A particularly preferred value of $R^3$ is the 1-hydroxyethyl group. A further particularly preferred value of $R^3$ is the $CH_3CH(OSO_3H)$-group. Both these values of $R^3$ occur in starting-materials that are readily available from natural sources.

Where applicable, the compounds of the formula (II) may have R or S sterochemistry at the C-8 position (that is the α-carbon atom of the C-6 substituent) or may be in the form of mixtures thereof. The compounds of the formula (II) wherein $R^3$ is a $CH_3CH(OSO_3H)$-group or methyl or ethyl ester thereof preferably have the S configuration at C-8 since the necessary starting-materials are more readily available.

The compounds of the formula (II) may be provided with a cis configuration of the C-5 and C-6 protons, or they may be provided with a trans configuration of the C-5 and C-6 protons (except for compounds wherein $R^3$ is $CH_3CH(OSO_3H)$ or a methyl or ethyl ester thereof). Alternatively the compounds of the formula (II) are provided as a mixture of the cis and trans forms.

In the sub-formula (b) above most suitably n is zero. Preferably the $C_{2-6}$ alkylene group is ethylene, trimethylene or tetramethylene, of these ethylene is preferred. In the sub-formula (c) most suitably $R^9$ is a hydrogen atom. Most suitably also $R^{10}$ is a hydrogen atom. Thus it is to be realised that favoured groups $X^1$ include $-S-CH_2-CH_2-$ and $-S-CH=CH-$.

In part B above suitable values of $X^1$ include $-SO-CH=CH-$ and $-S-C(Br)=CH-$.

In part C above suitable values of $X^1$ include $-SO-CH_2-CH_2-$, $-S-CH=CH-$, $-SO-CH=CH$, $-S-C(Br)=CH$ and $-SO-C(Br)=CH-$, of these $-SO-CH_2-CH_2-$, $-SCH=CH-$ and $-SO-CH=CH-$ are preferred.

If a double bond is present in the group X then this may be in the E or Z configuration.

From the foregoing it will be realised that favoured compounds of this invention include those of the formulae (IV)–(VII):

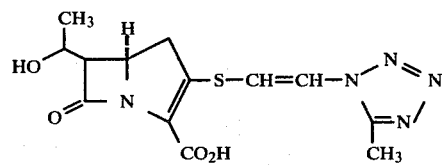

(IV)

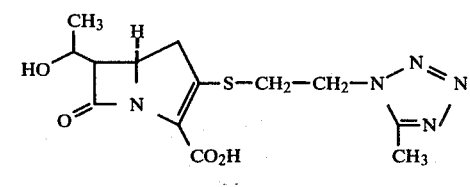

(V)

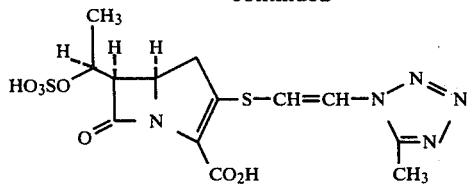
(VI)

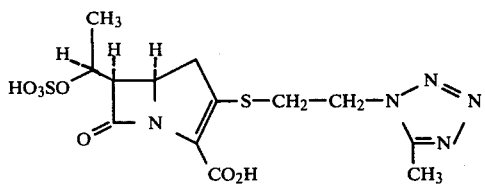
(VII)

and pharmaceutically acceptable salts and in-vivo hydrolysable esters thereof.

In another aspect favoured compounds of this invention are those of the formulae (IV)–(VII) wherein the methyl substituent of the tetrazole ring is replaced by an aminomethyl substituent.

The compounds of the formulae (II)–(VII) most suitably may be presented in the form of the carboxylic free acid at the C-2 position, said compounds preferably being in zwitterionic form. Alternatively the compounds of the formulae (II)–(VII) may be in the form of a salt such as an alkali metal salt, an alkaline earth metal salt or an ammonium or substituted ammonium salt. Suitable salts thus include the sodium, potassium, calcium, magnesium, ammonium and trimethylammonium salts. Of these the preferred salts are the sodium and potassium salts.

If a carboxylic acid function is present in the group $R^4$ then this may be in the form of the free acid or a pharmaceutically acceptable salt thereof. Alternatively a carboxylic acid function in the group $R^4$ may be present in the form of an ester, for example as a $C_{1-6}$ alkyl ester optionally substituted by $C_{1-6}$ alkoxy or by phenyl or by phenyl substituted by chlorine, bromine, fluorine, nitro, $C_{1-3}$ alkyl, $C_{1-3}$ alkoxy, $C_{1-3}$ acyloxy or $C_{1-3}$ alkoxycarbonyl. Thus suitable ester grouping within $R^4$ include methyl, ethyl, propyl, butyl, benzyl, p-nitrobenzyl, methoxymethyl and benzhydryl.

Compounds of the formulae (II), (III), (VI) and (VII) containing a $CH_3CH(OSO_3H)$-group at C-6 are normally and preferably provided in the form of a pharmaceutically acceptable salt of that group. Thus compounds of the formulae (II), (III), (VI) and (VII) may exist in the form of a pharmaceutically acceptable salt of a zwitterion, for example the mono-sodium salt.

The compounds of the formulae (II), (III), (VI) and (VII) containing a $CH_3CH(OSO_3H)$-group in the form of its methyl or ethyl sulphate ester are primarily envisaged as intermediates.

Suitable esters of the compounds of the invention include those convertible to the free acid or salt thereof by biological methods such as enzymatic hydrolysis and in-vivo hydrolysis, and those convertible by chemical methods such as hydrogenolysis, hydrolysis, electrolysis or photolysis.

Suitably the esterifying group is an alkyl, alkenyl, aryl or aralkyl group which may be substituted if desired. Preferably the alkyl, alkenyl and alkynyl groups and the alkyl portion of the aralkyl group contain up to 6 carbon atoms. Suitable substituents which may be included in the esterifying group include halogen atoms and $C_{1-6}$ alkoxy, $C_{1-6}$ alkanoyl, hydroxy, $C_{1-6}$ acyloxy for example $C_{1-6}$ alkanoyloxy, $C_{1-6}$ alkylamino and di($C_{1-6}$)alkylamino groups.

More suitably the carboxylic acid is esterified by a group of the sub-formula (k), (l), (m), (n), (p) or (q):

(k)

(l)

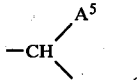
(m)

(n)

(p)

(q)

wherein $A^1$ is a hydrogen atom, $C_{1-6}$ alkanoyl or an $C_{1-5}$ alkyl group optionally substituted by $C_{1-7}$ alkoxy or $C_{1-7}$ carboxylic acyloxy, or an alkenyl or alkynyl group of up to 5 carbon atoms; $A^2$ is a hydrogen atom or a methyl group; $A^3$ is a phenyl group or a phenyl group substituted by a fluorine, chlorine or bromine atom or a nitro, $C_{1-3}$ alkyl or $C_{1-3}$ alkoxy group; $A^4$ is a hydrogen atom or a phenyl group or phenyl group substituted by a fluorine, chlorine or bromine atom or a nitro, $C_{1-3}$ alkyl or $C_{1-3}$ alkoxy group; $A^5$ is a hydrogen atom or a methyl group; $A^6$ is a $C_{1-6}$ alkyl, phenyl, phenoxy, phenyl ($C_{1-3}$) alkyl, phenyl ($C_{1-3}$) alkoxy or $C_{1-6}$ alkoxy group or $A^5$ is joined to $A^6$ to form a phthalidyl, dimethylphthalidyl or dimethoxyphthalidyl group; $A^7$ is a $C_{1-4}$ alkyl, phenyl, chlorophenyl or nitrophenyl group; $A^8$ is a $C_{1-4}$ alkyl or phenyl group; $A^9$ is a $C_{1-4}$ alkyl or phenyl group; $A^{10}$ is $C_{1-4}$ alkyl; and $A^{11}$ is $C_{1-4}$ alkyl: or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group. Favourably $A^5$ is a hydrogen atom.

Preferred groups of the sub-formula (k) include the methyl, ethyl and acetonyl groups.

Preferred groups of the sub-formula (l) include the benzyl and p-nitrobenzyl groups.

When $A^5$ is hydrogen, suitably $A^6$ is selected from methyl, ethyl, n-propyl, iso-propyl, n-butyl, tert-butyl, phenyl, benzyl, methoxy, ethoxy, n-propyloxy and iso-propyloxy. Preferably $A^6$ is tert-butyl. Preferred groups of the sub-formula (m) include the acetoxymethyl, pivaloyloxymethyl, ethoxycarbonyloxymethyl, phthalidyl, α-ethoxycarbonyloxyethyl and α-acetoxyethyl groups. These esterifying groups are favoured as they tend to form in-vivo hydrolysable esters.

A preferred group of the sub-formula (n) is the methoxymethyl group.

Preferred groups of the sub-formula (p) include the trimethylsilyl, tert-butyldimethylsilyl and tert-butyldiphenylsilyl groups.

A preferred group of the sub-formula (q) is p-methoxycarbonylbenzyl.

Particularly preferred esterifying groups are the p-nitrobenzyl and phthalidyl groups.

The in-vivo hydrolysable nature of the ester may be confirmed by administration to an animal such as a mouse or rat and determination of the presence of a compound of the formula (II) or a salt thereof in the blood or urine of the animal. Alternatively hydrolysis in human blood or serum may be determined.

The compounds of the formulae (II)-(VII), their pharmaceutically acceptable salts and esters, for example in-vivo hydrolysable esters, may be employed in the treatment of bacterial infection. Thus the present invention also provides a pharmaceutical composition which comprises a compound of the formulae (II)-(VII) or a pharmaceutically acceptable salt or ester thereof and a pharmaceutically acceptable carrier. Preferably any ester is in-vivo hydrolysable.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections inter alia of the respiratory tract, urinary tract or soft tissues in humans, or mastitis in cattle. Such compositions may be administered to susceptible gram-positive or gram-negative bacteria such as strains of *Staphylococcus aureus, Klebsiella aerogenes* and *Escherichia coli.*

The carriers used in the compositions of this invention may include diluents, binders, disintegrants, lubricants, colours, flavouring agents and preservatices in conventional manner. Thus suitable agents include lactose, starch, sucrose, calcium phosphate, sorbitol, polyvinylpyrrolidone, acacia, gelatin, tragacanth or the like, potato starch or polyvinylpolypyrrolidone, magnesium stearate and sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin and mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride, bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusions in the injectably administrable compositions of this invention include cefazolin and cephradine, generally as their pharmaceutically acceptable salt such as the sodium salt. Cephaloridine is also particularly suitable for inclusion in injectably administrable compositions.

The weight ratio between compound of this invention and penicillin or cephalosporin is generally from 10:1 to 1:10, for more usually from 5:1 to 1:5 and normally from 3:1 to 1:3.

The penicillin or cephalosporin is generally utilised in its conventionally administered amount.

There is also provided a process for the preparation of a compound of the formula (II) or salt or ester thereof which process comprises the reaction of a compound of the formula (VIII):

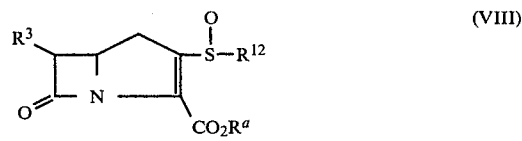

wherein $R^3$ is as hereinbefore defined, $R^{12}$ is an organic group bonded via a carbon atom and $R^a$ is a carboxy-blocking group or a hydrogen atom; and a compound of the formula (IX):

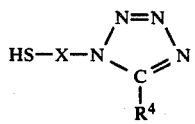

(IX)

or reactive derivative thereof, wherein X and R$^4$ are as hereinbefore defined in relation to formula (II); and thereafter if necessary:

(i) removing any carboxy-blocking group R$^a$,
(ii) converting the product into a pharmaceutically acceptable salt or ester,
(iii) oxidising the sulphur atom to afford a compound wherein n is one.

This process may be carried out in any solvent that is substantially inert during the reaction for example tetrahydrofuran, dimethylformamide, dioxan, hexamethyl phosphoramide, dimethoxyethane or dimethoxydiethyl ether. Of these solvents dimethylformamide is preferred.

Alternatively we have found it useful to use a phase transfer catalyst. Particularly suitable phase transfer catalysts include tetra-n-butyl ammonium bromide, cetyl bromide and cetyltriethyl ammonium chloride and cetyl benzyl dimethylammonium chloride. Suitable solvents include halogenated water-immiscible solvents such as chloroform or dichloromethane in the presence of water.

The reaction is normally performed at ambient or a depressed temperature, for example 20° C. to −70° C., and preferably between 0° C. and −50° C. However when using a phase transfer catalyst it is preferable to conduct the reaction between 0° C. and ambient temperature.

When the thiol compound of the formula (IX) is used, the reaction is normally carried out in the presence of a base. Examples of such bases include sodium hydride, sodium, hydroxide, sodium alkoxide such as the methoxide, ethoxide or butoxide, sodium amide, potassium hydroxide, potassium alkoxide such as the methoxide, ethoxide or butoxide, potassium amide, and trialkylamines such as triethylamine and tri-n-propylamine. Of these triethylamine is preferred. Preferably the base is present in an amount of at least 0.9 equivalents, more preferably between 1.0 and 1.2 equivalents, per mole of the thiol compound.

Instead of using a base in the reaction, a reactive derivative of the thiol may be used, preferably the reactive derivative is a salt of the thiol, in particular an alkali metal salt such as sodium, potassium or lithium.

The amount of thiol compound of the formula (IX) or reactive derivative thereof is generally between 1.0 and 1.5 moles per mole equivalent of the compound of the formula (VIII).

The group R$^{12}$ in the compound of the formula (VIII) may be C$_{1-6}$ alkyl, C$_{2-6}$ alkenyl, C$_{2-6}$ alkynyl, aryl (C$_{1-6}$) alkyl, C$_{1-6}$ alkanoyl, aryl (C$_{1-6}$) alkanoyl, arylcarbonyl, aryl, heterocyclyl, heterocyclyl (C$_{1-6}$) alkyl, heteroaryl (C$_{1-6}$) alkyl or heteroaryl group, any of such groups being optionally substituted. Suitably the hetero atom or hetero atoms in the above named heteroaryl and/or heterocyclyl moieties are selected from 1 to 4 oxygen, nitrogen or sulphur atoms.

Suitable optional substituents for the group R$^{12}$ include amino, alkanoylamino, mono, di- and trialkylamino, hydroxy, alkoxy, mercapto, alkylthio, arylthio, sulphamoyl, carbamoyl, amidino, guanidino, nitro, chloro, bromo, fluoro, carboxy and salts and esters thereof, alkanoyloxy, arylcarbonyl and heteroarylcarbonyl.

Suitably R$^{12}$ is C$_{1-6}$ alkyl, C$_{2-6}$ alkenyl, aryl such as phenyl, aralkyl wherein the aryl moiety is preferably phenyl and the alkyl part has 1 to 6 carbon atoms, for example benzyl, phenethyl; heterocyclyl or heterocyclylalkyl wherein the alkyl part has 1 to 3 carbon atoms and the heterocyclic ring comprises 4 to 7 atoms, preferably 5 to 6, up to 4 of which may be selected from oxygen, sulphur and nitrogen, such as pyridyl, furyl, thienyl, pyrimidinyl, imidazolyl, triazinyl and tetrazolyl.

Preferably R$^{12}$ is C$_{1-6}$ alkyl for example methyl, ethyl or propyl, optionally substituted by amino, alkanoylamino, carboxy, mono- and di-alkylamino, hydroxy or C$_{1-6}$ alkoxy; C$_{2-6}$ alkenyl such as vinyl optionally substituted with alkanoylamino such as acetamido; or is an optionally substituted phenyl, pyrimidinyl or pyridyl group.

Suitable carboxyl-blocking derivatives for the group —CO$_2$R$^a$ in formula (VIII) include salts, esters, and anhydride derivatives of the carboxylic acid. The derivative is one which may readily be cleaved at a later stage of the reaction. The salts need not be pharmaceutically acceptable. Suitable salts include inorganic salts, for example metal salts such as silver or mercuric salt, or alkali metal salts such as the lithium or sodium salt, tertiary amine salts, such as those with tri-lower-alkylamines, N-ethylpiperidine, dimethylpiperazine. A preferred salt is with triethylamine. Also of use are quaternary ammonium salts such as tetrabutylammonium.

Suitable ester-forming carboxyl-blocking groups are those which may be removed under conventional conditions. Such groups for R$^a$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=CHR$^b$ where R$^b$ is aryl or hetero-cyclic, or an in vivo hydrolysable ester.

The carboxyl group may be regenerated from any of the above esters by usual methods appropriate to the particular R$^a$ group, for example, acid- and base-catalysed hydrolysis, or by enzymically-catalysed hydrolysis, or by hydrogenation. The hydrolysis must of course be carried out under conditions to which the groups on the rest of the molecule are stable.

When it is desired to produce a compound of formula (II) in the form of a free acid or salt by this process a compound of formula (VIII) is generally employed wherein R$^a$ is a carboxyl-blocking group. For the preparation of a compound of formula (II) in the form of a pharmaceutically acceptable ester, it is convenient to employ a compound of formula (VIII) wherein R$^a$ represents the desired ester group.

Preferably this process is performed on a compound of the formula (VIII) wherein R$^a$ is an ester-forming group.

Suitable esters of the compounds of the formula (VIII) for use in this process include those cleavable by biological methods and by chemical methods such as hydrogenolysis, hydrolysis, electrolysis or photolysis.

Suitably the carboxylic acid is esterified by a group of the sub-formula (k), (l), (m), (n), (p) or (q) as hereinbefore defined.

The oxidation of a compound of the formula (II) wherein n is zero to a compound of the formula (II) wherein n is one may be performed by use of an oxidising agent. Suitable oxidising agents include perbenzoic acid, hydrogen peroxide, iodobenzene dichloride/water and sodium metaperiodate. Substituted perbenzoic acids such as m-chloroperbenzoic acid are preferred. The oxidation is conveniently performed in an inert solvent such as dichloromethane, chloroform/ethanol, aqueous dioxan, chloroform or carbon tetrachloride at an ambient or depressed temperature, preferably between $-30°$ C. and $+20°$ C. The amount of the oxidising agent used can vary dependent on the type of agent, reaction conditions, presence of other potentially reactive groups, etc. Generally between 1 and 2 molar equivalents of the oxidising agent are preferred.

The present invention also provides a process for the preparation of a compound of the formula (III) or pharmaceutically acceptable salt or ester thereof which process comprises the reaction of azide ion with a compound of the formula (X):

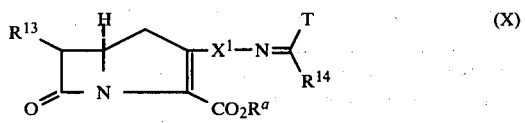

(X)

wherein $R^{13}$ and $R^{14}$ are respectively either groups $R^3$ and $R^4$ as hereinbefore defined in relation to formula (III) or are groups that on chemical cleavage afford groups $R^3$ and $R^4$; $X^1$ and $R^a$ are as hereinbefore defined, T is a bromine or chlorine atom; and thereafter if necessary performing one or more of the following steps:

(i) removing any carboxy-blocking group $R^a$, (ii) converting the product into a pharmaceutically acceptable salt or ester, (iii) oxidising the sulphur atom to afford a compound wherein n is one, (iv) converting any group $R^{13}$ to $R^3$ and any group $R^{14}$ to $R^4$.

The reaction is suitably performed in an inert organic solvent such as dimethylformamide, dichloromethane and chloroform.

The reaction may be carried out at a non-extreme temperature such as $-60°$ C. to $+60°$ C., preferably from $-20°$ C. to $+40°$ C., more preferably from $0°$ C. to $+30°$ C. and conveniently at ambient temperature.

The azide ion may be introduced to the reaction as an inorganic azide such as sodium azide, or as an organic azide such as tetramethylguanidium azide. Care must be exercised when selecting an appropriate azide as many azides, particularly heavy metal azides, are explosive.

When it is desired to prepare a compound of the formula (II) or salt or ester thereof wherein there is a $NH_2$ substitutent in the group $R^4$, the amino group may be protected in conventional manner during the reaction. Suitable protecting groups include organic silyl groups such as tri-$C_{1-4}$ alkylsilyl groups for example the trimethylsilyl group. If there is a —OH substituent in the group $R^3$ or $R^4$ then this may be protected in conventional manner during the reaction. Suitable protecting groups include the benzyloxycarbonyl and p-nitrobenzyloxycarbonyl groups, which may be removed conventionally, for example by catalytic hydrogenation.

Suitable methods of hydrogenolysis of esters of the compounds of the formula (II) include hydrogenation in the presence of a transition metal catalyst. Suitable hydrogenolysable esters of the compounds of the formula (II) include those where the ester moiety is of the sub-formula: $CO_2CHR^{18}R^{19}$ wherein $R^{18}$ is an alkenyl group of up to 5 carbon atoms or is a phenyl group optionally substituted by a fluorine, chlorine or bromine atom, or a nitro or alkyl or alkoxy group of up to 4 carbon atoms; and $R^{19}$ is a hydrogen atom, an alkyl group of up to 4 carbon atoms or a phenyl group optionally substituted by a fluorine, bromine or chlorine atom, or a nitro or alkyl or alkoxy group of up to 4 carbon atoms.

Of these hydrogenolysable esters the substituted benzyl esters are preferred. The p-nitrobenzyl ester is particularly favoured.

The pressure of hydrogen used in the hydrogenation step may be low, medium or high, but in general an approximately atmospheric or slightly superatmospheric pressure is preferred. The transition metal catalyst employed is preferably palladium for example palladium on charcoal, palladium on barium sulphate or palladium on calcium carbonate. The hydrogenation may be effected in any convenient solvent in which the compound is soluble such as tetrahydrofuran, dioxan, ethanol, or such solvents in mixture with water. Phosphate buffer may also be included in the hydrogenation medium.

If the hydrogenation is carried out in the presence of a base then a salt of a compound of the formula (II) is produced. Suitable bases include sodium bicarbonate, sodium carbonate, potassium carbonate, calcium carbonate and lithium carbonate. If no base is present then the hydrogenation leads to the preparation of an acid of a compound of the formula (II) which may then be neutralised if desired to yield a salt, such neutralisation being effected in conventional manner.

Suitable ester groups removable by mild hydrolysis include silyl esters such as the trimethylsilyl, tert-butyldimethylsilyl and tertbutyldiphenylsilyl esters. In general such esters are prepared by the reaction of a carboxylic acid salt with the appropriate silyl chloride.

Re-esterification of a carboxyl group of a salt of a compound of the formula (II) may be effected in conventional manner. Suitable methods include the reaction of an alkali metal salt of the compound of the formula (II) such as the sodium or potassium salt with a reactive halide or sulphonate ester such as a bromide, chloride, mesylate or tosylate. Such esterifications may be carried out under conventional conditions for example in dimethylformamide at room temperature.

A compound of the formula (X) may be prepared by a process which comprises the reaction of a corresponding a compound of the formula (XI):

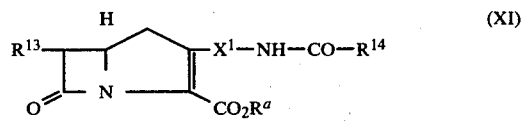

(XI)

wherein $R^{13}$, $R^{14}$, $R^a$ and $X^1$ are as defined in relation to formula (X), with an imino-halogenating agent and a base.

The imino-halogenating agent used is one which will convert an amide group —NH—CO— to an iminohalide group —N=CT— wherein T is as defined in relation to a compound of the formula (X) for example, phosphorus pentachloride, phosphorus pentabromide, thionyl chloride, thionyl bromide, phosgene, phosphorus trichloride, phosphorus tribromide, phosphorus oxychloride and phosphorus oxybromide.

The solvent used is suitably an inert organic solvent such as dichloromethane, chloroform, carbon tetrachloride, dichloroethane, tetrahydrofuran or dioxan.

The reaction is performed in the presence of a base. Suitably the base is an organic base is an organic base for example a tertiary amine such as triethylamine, trimethylamine or N-alkyl-morpholine, and pyridine. Most suitably the organic base is N-methylmorpholine.

We have also found it possible to use triphenylphosphine or tri-p-methoxyphenylphosphine with carbon tetrahalide as an iminohalogenating agent for example triphenylphosphine in carbon tetrachloride or triphenylphosphine and carbon tetrabromide in an organic solvent, for example, dichloromethane, chloroform or benzene.

The compounds of the formula (XI) may be prepared by the methods described in European Patent Application Publication Nos.: 0002564, 0003740, 0005348, 0005349, 0007753, 0007152, 0008497, 0008888; West German OSL Nos. 2728097 and 2724560; Belgian Pat. No. 864570; U.K. Pat. Nos.: 1489235, 1483142, 1467413; Co-pending U.K. Patent Application Nos.: 7947458 and 8002105 and European Patent Application No. 81302588.9

The following examples illustrate this invention.

EXAMPLE 1

Preparation of p-Nitrobenzyl (5R, 6R)-3-[2-(5-Methyltetrazol-1-yl)ethylthio]-6-[(1S)-1-trimethylsilyloxyethyl]-7-oxo-1-azabicyclo[3.2.0]hept-2-ene-2-carboxylate

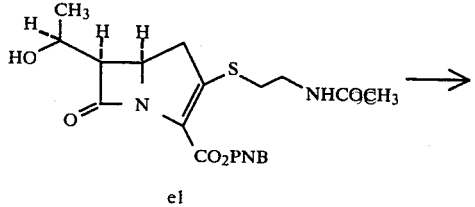

e1

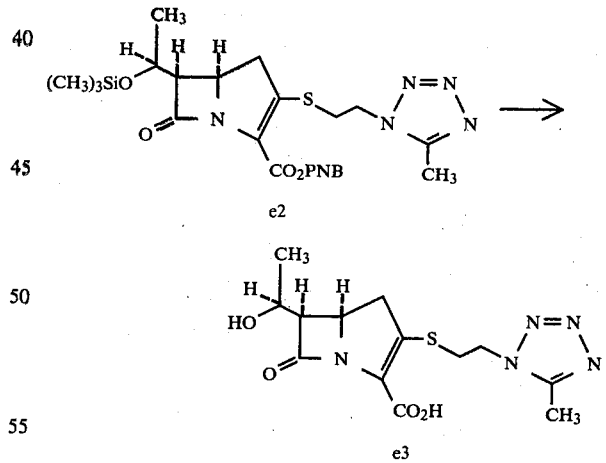

e2

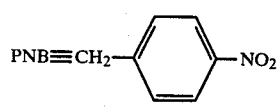

p-Nitrobenzyl (5R, 6R)-3-(2-acetamidoethylthio)-6-[(1S)-1-hydroxyethyl]-7-oxo-1-azabicyclo[3.2.0]hept-2-ene-2-carboxylate, e1 (232 mg) was suspended in pyridine (3 ml) and treated with chlorotrimethylsilane (350 mg). After 15 min. the pyridine was evaporated in vacuo and ethyl acetate (20 ml) and water (20 ml) were added to the residue. After shaking, the layers were separated and the ethyl acetate layer was washed with brine, dried (MgSO$_4$) and evaporated in vacuo. Toluene (10 ml) was added to the residue and evaporated in vacuo. The resultant trimethylsilyl ether was taken up in dry dichloromethane (6 ml), cooled to −30° and N-methylmorpholine (0.25 ml) was added. A solution of phosgene in toluene (0.90 ml; 12.5% w/w, d 0.91), diluted with dry CH$_2$Cl$_2$ (1 ml), was added dropwise. The mixture was allowed to warm to room temperature and the i.r. spectrum of the reaction mixture indicated that the imidoyl chloride had formed. Tetramethylguanidinium azide in dichloromethane (0.90 ml, 100 mg/ml) was added and after stirring at room temperature for 15 min. a further portion (0.20 ml) of the azide solution was added, and after another 15 min. more azide solution (0.15 ml) was added. After 15 min. the solution was diluted with dichloromethane (15 ml), water (15 ml) was added, the layers separated and the dichloromethane layer was washed with brine, dried (MgSO$_4$) and evaporated in vacuo to dryness. Toluene (2×20 ml) was added to the residue and evaporated in vacuo. The product was chromatographed on silica gel (230–400 mesh ASTM) (15 g) eluting with ethyl acetate to give, after combination and evaporation of appropriate fractions, the title compound, e2, (210 mg), $\lambda_{max}$ (EtOH) 311 ($\epsilon$10932) and 265 (11509) nm, $\nu_{max}$ (CH$_2$Cl$_2$) 1785, 1705, 1525, 1345, 1150, 845 cm$^{-1}$, [M+ found m/e 546.1677; C$_{23}$H$_{30}$N$_6$O$_6$SSi requires m/e 546.1714].

EXAMPLE 2

Preparation of (5R, 6R)-6-[(1S)-1-Hydroxyethyl]-3-[2-(5-methyltetrazol-1-yl)ethylthio]-7-oxo-1-azabicyclo[3.2.0]hept-2-ene-2-carboxylic acid

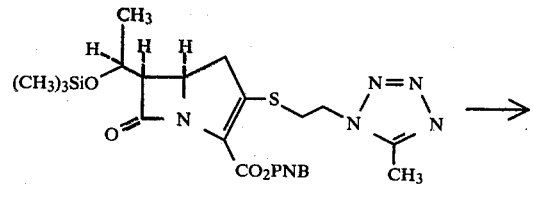

e2

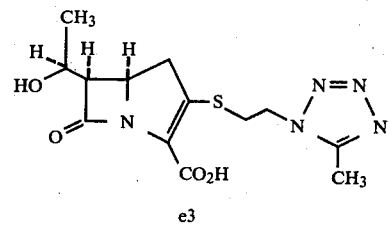

e3

The ester, e2, (186 mg) in dioxan (16 ml) and aqueous pH 7 0.05 M phosphate buffer solution (8 ml) was hydrogenated at atmospheric pressure over 5% palladium on carbon catalyst (300 mg) for 2 hours. The catalyst was filtered off by filtration through Celite and the filter cake was washed with water. The volume of filtrate was now ca 200 ml. The volume of the solution was reduced to ca 100 ml by evaporation in vacuo. Water (100 ml) was added and the solution was washed with ethyl acetate (4×200 ml). The volume of the aqueous layer was then reduced to 70 ml and a u.v. assay (assuming $\epsilon_{295}$ 8,500) indicated the presence of 59 mg (49% yield) of the acid (or the corresponding zwitterion), e3.

The volume of the solution to ca 7 ml and this solution was loaded onto Biogel P-2 (12×2 cm) and the column was eluted with water.

Fractions containing a u.v. chromophore at 295–297 nm were combined, the volume of water reduced by evaporation in vacuo and the resultant solution was freeze dried to give (5R, 6R)-6-[(1S)-1-hydroxyethyl]-3-[2-(5-methyltetrazol-1-yl)ethylthio]-7-oxo-1-azabicyclo[3.2.0]hept-2-ene-2-carboxylic acid, e3, $\lambda_{max}$ (H$_2$O) 295 nm; $\nu_{max}$ (KBr) 1750, 1600 cm$^{-1}$.

EXAMPLE 3

Preparation of p-Nitrobenzyl (5R, 6R)-3-[2-(5-Methyltetrazol-1-yl)ethylthio]-6-[sodium (1S)-1-sulphonatooxyethyl]-7-oxo-1-azabicyclo[3.2.0-]hept-2-ene-2-carboxylate

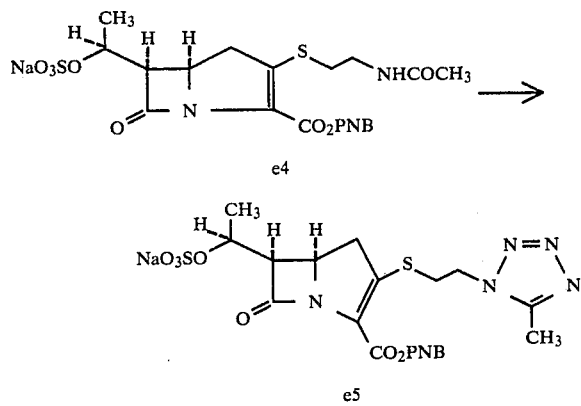

p-Nitrobenzyl (5R, 6R)-3-(2-acetamidoethylthio)-6-[sodium (1S)-1-sulphonatooxyethyl]-7-oxo-1-azabicyclo[3.2.0]hept-2-ene-2-carboxylate (275 mg), e4 in water (20 ml) was treated with benzyldimethyl-n-hexadecylammonium chloride (203 mg) in dichloromethane. After shaking and separation the aqueous layer was re-extracted with dichloromethane (30 ml). The dichloromethane extracts were combined, dried (MgSO$_4$) and evaporated to dryness, Toluene (2×20 ml) was added to the residue and removed in vacuo to give the quaternary ammonium salt corresponding to the starting material. The quaternary-ammonium salt was dissolved in dry dichloromethane (6 ml), treated with N-methylmorpholine (0.30 ml; 0.27 g) and the mixture was cooled to −30° and a solution of phosgene in toluene (1.0 ml; 12.5% w/w, d 0.91; 0.114 g COCl$_2$), diluted with dichloromethane (1 ml), was added. The mixture was allowed to warm to room temperature to give the imidoyl chloride [$\nu_{max}$ (CH$_2$Cl$_2$) 1780 and 1700 cm$^{-1}$].

Tetramethylguanidinium azide in dichloromethane (1.0 ml; 100 mg/ml) was added and the mixture was stirred for 20 min. when more of the tetramethylguanidinium azide solution (0.25 ml) was added. After 3 min. dichloromethane (50 ml) was added and the solution was washed with water (2×30 ml), followed by saturated brine (15 ml). The dichloromethane solution was then dried (MgSO$_4$), evaporated in vacuo, toluene (20 ml) was added to the residue and evaporated in vacuo. The residual oil was re-dissolved in dichloromethane, evaporated in vacuo and then dried under high vacuum to give the quaternaryammonium salt corresponding to e5 as a solid, $\nu_{max}$(CH$_2$Cl$_2$) 1780, 1700 cm$^{-1}$. The quaternaryammonium salt corresponding to e5 was chromatographed on a silica gel column (14×2.3 cm), eluting with chloroform/ethanol mixtures; 4:1 (50 ml); 7:3 (50 ml); 65:35 (50 ml); 3:2. Eventually the desired salt eluted, and fractions containing the salt were combined and evaporated in vacuo. Chloroform (3×30 ml) was added to the residue and evaporated in vacuo to give the purified quaternary ammonium salt corresponding to e5, $\nu_{max}$ (CH$_2$Cl$_2$) 1780, 1700, 1525, 1350 cm$^{-1}$. The salt was dissolved in acetone (2 ml) and sodium iodide (32 mg) in acetone (0.5 ml) was added but as the desired sodium salt did not precipitate the acetone was removed in vacuo and dichloromethane was added to the residue to give a solid which was collected by filtration, washed with dry ether, and then dried under high vacuum. The resultant solid (151 mg) was suspended in chloroform/ethanol (3:2, 3 ml) containing N,N-dimethylformamide and loaded onto a silica gel column (8.5×2.3 cm) and the column was then eluted with chloroform/ethanol mixtures; 7:3 (50 ml) then 3:2. Fractions containing the product e5 were combined and evaporated in vacuo. Toluene (3×10 ml) was added to the residue and evaporated in vacuo. Ether was then added to the residue and the solid was filtered off to give p-nitrobenzyl (5R, 6R)-3-[2-(5-methyltetrazol-1-yl)ethylthio]-6-[sodium (1S)-1-sulphonatooxyethyl]-7-oxo-1-azabicyclo[3.2.0-]hept-2-ene-2-carboxylate, e5, (105 mg), $\nu_{max}$ (H$_2$O) 309 ($\epsilon$9,755) and 274 (9645) nm, $\nu_{max}$ (KBr) 1770, 1700 cm$^{-1}$, $\delta$[(CD$_3$)$_2$NCDO]1.48 (3H, d), 2.63 (3H, s), 3.1–4.7 (m), 4.79 (2H, broad t, J 7 Hz), 5.23 and 5.54 (2H, ABq, J 14 Hz), 7.79 (2H, d, J 9 Hz), 8.17 (2H, d, J 9 Hz).

EXAMPLE 4

Mono Sodium Salt of (5R, 6R)-6-[(1S)-1-Hydroxysulphonyloxyethyl]-3-[2-(5-methyltetrazol-1-yl)ethylthio]-7-oxo-1-azabicyclo[3.2.0]hept-2-ene-2-carboxylic acid

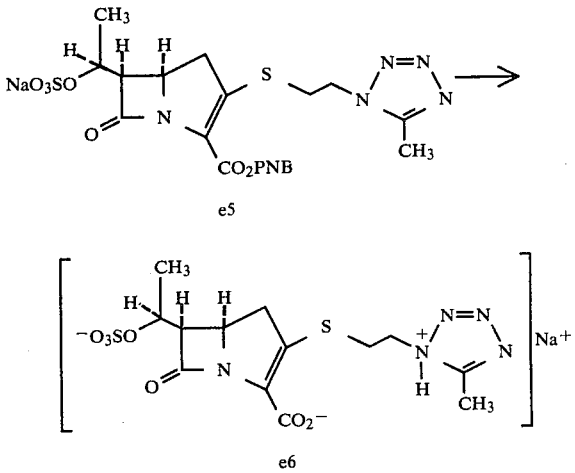

The ester e5 (90 mg) was added to 5% palladium on carbon catalyst (previously hydrogenated for 15 min) in dioxan (10 ml) and aqueous pH 7 0.05 M phosphate buffer solution (5 ml) and the mixture was hydrogenated for 2½ hours. The catalyst was filtered off and washed with water (100 ml). The volume of filtrate and washings were reduced to ca 50 ml by evaporation in vacuo and the solution was then extracted with ethyl acetate (3×50 ml). The solution was diluted with a little water and any volatile materials were removed by evaporation in vacuo for a short time, and then the volume of the aqueous solution was reduced to ca 20 ml by evaporation in vacuo and the material was then freeze dried to give the sodium salt of (5R, 6R)-6-[(1S)-1-hydroxy-sulphonyloxyethyl]-3-[2-(5-methyltetrazol-1-yl)ethylthio]-7-oxo-1-azabicyclo[3.2.0]hept-2-ene-2-carboxylic acid, e5, $\nu_{max}$ (H$_2$O) 295 nm, $\nu_{max}$ (KBr) 1755, 1600 cm$^{-1}$.

EXAMPLE 5

Preparation of p-Nitrobenzyl (5R, 6S)-3-[2-(5-Methyltetrazol-1-yl)ethylthio]-6-[(1S)-1-trimethylsilyloxyethyl]-7-oxo-1-azabicyclo[3.2.0]hept-2-ene-2-carboxylate

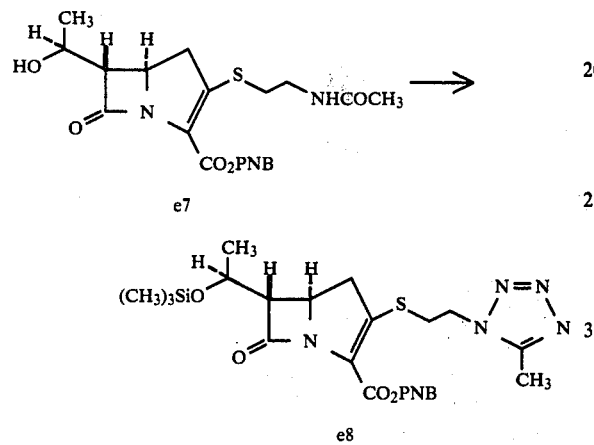

p-Nitrobenzyl (5R, 6S)-3-(2-acetamidoethylthio)-6-[(1S)-1-hydroxyethyl]-7-oxo-1-azabicyclo[3.2.0]hept-2-ene-2-carboxylate, e7, (120 mg) was suspended in pyridine (2 ml) and treated with chlorotrimethylsilane (210 mg). After 15 minutes the pyridine and excess reagent were evaporated in vacuo and ethyl acetate and water were added to the residue. After separation the ethyl acetate layer was washed with water, followed by brine, dried (MgSO$_4$) and evaporated in vacuo. Toluene was added to the residue and evaporated in vacuo to give the trimethylsilyl ether corresponding to the starting material. The trimethyl silyl ether was taken up in dry dichloromethane (3 ml), treated with N-methylmorpholine (0.117 ml), the mixture was cooled to $-30°$ and a solution of phosgene in toluene (0.46 ml, 12.5% w/w; 52 mg COCl$_2$), diluted to 2 ml by dry dichloromethane was added dropwise. The mixture was permitted to warm to room temperature, and after 10 minutes the i.r. spectrum of the mixture indicated formation of the imidoyl chloride. Tetramethylguanidinium azide (45 mg) was added and the mixture was stirred for 20 minutes and then more tetramethylguanidinium azide (15 mg) was added. After 15 minutes the mixture was worked up by dilution to 20 ml with dichloromethane and addition of water (15 ml). After separation the dichloromethane layer was washed with water (15 ml), then with brine (15 ml), dried (MgSO$_4$) and evaporated in vacuo. The crude product was then chromatographed on silica gel (230–400 mesh ASTM 8 g), eluting with ethyl acetate. The fractions containing the product (74 mg) were combined and evaporated in vacuo. Crystallisation of the product from ethyl acetate/cyclohexane yielded colourless crystals of p-nitrobenzyl (5R, 6S)-3-[2-(5-methyltetrazol-1-yl)ethylthio]-6-[(1S)-1-trimethylsilyloxyethyl]-7-oxo-1-azabicyclo[3.2.0]hept-2-ene-2-carboxylate, e8, m.p. 178°–180°, $\nu_{max}$ (EtOH) 315 ($\epsilon$12446) and 266 (11557) nm, $\nu_{max}$ (CH$_2$Cl$_2$) 1780, 1705, 1525, 1335, 1195, 1130 and 845 cm$^{-1}$. [Found M+m/e 546.1692; C$_{23}$H$_{30}$N$_6$O$_6$SSi requires m/e 546.1714].

EXAMPLE 6

Preparation of (5R, 6S)-3-[2-(5-Methyltetrazol-1-yl)ethylthio]-6-[(1S)-1-hydroxethyl]-7-oxo-1-azabicyclo[3.2.0]hept-2-ene-2-carboxylic acid

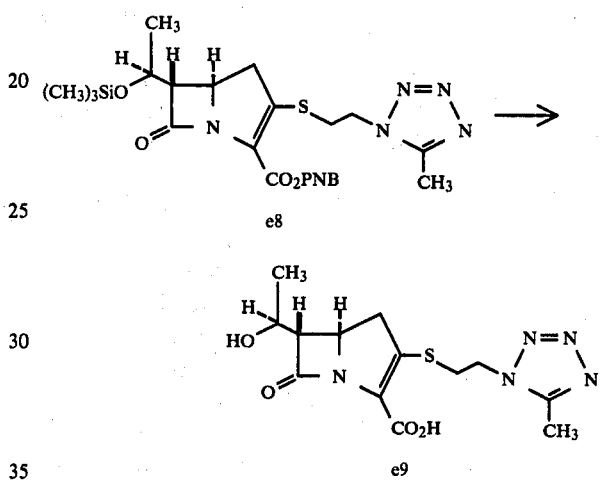

The ester, e8, (56 mg) in dioxan (3 ml) was added to prehydrogenated (15 min) 5% palladium on carbon catalyst (135 mg) in dioxan (10 ml) and aqueous pH 7 0.05 M phosphate buffer solution (5 ml) and the mixture was hydrogenated for 2.5 hr. The catalyst was filtered off and washed with water (100 ml). The solution was worked up by a similar procedure to that described in Example 4 to give (5R, 6S)-3-[2-(5-methyltetrazol-1-yl)ethylthio]-6-[(1S)-1-hydroxyethyl]-7-oxo-1-azabicyclo[3.2.0]hept-2-ene-2-carboxylic acid, e9, $\nu_{max}$ (H$_2$O) 297 nm; $\nu_{max}$ (KBr) 1760, 1600 cm$^{-1}$, as a freeze-dried solid.

EXAMPLE 7

Preparation of p-Nitrobenzyl (5R, 6S)-3-[(E)-2-(5-Methyltetrazol-1-yl)ethenylthio]-6-[(1S)-1-trimethylsilyloxyethyl]-7-oxo-1-azabicyclo[3.2.0]hept-2-ene-2-carboxylate

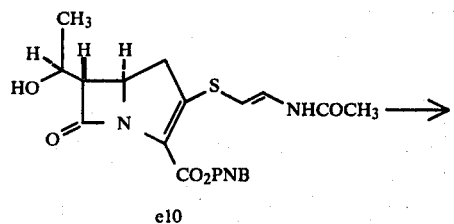

-continued

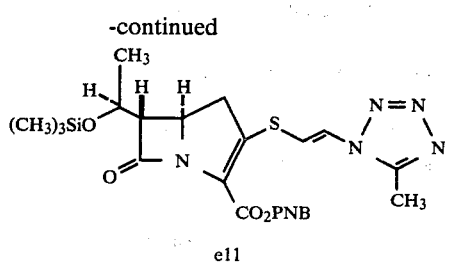

e11 p-Nitrobenzyl (5R, 6S)-3-[(E)-2-acetamidoethenylthio]-6-[(1S)-1-hydroxyethyl]-7-oxo-1-azabicyclo[3.2.0-]hept-2-ene-2-carboxylate, e10, (230 mg) in pyridine (3ml) was treated with chlorotrimethylsilane (350 mg). After 15 min., more chlorotrimethylsilane (150 mg) was added and after a further 5 min. the pyridine and excess chlorotrimethylsilane were removed by evaporation in vacuo. The residue was taken up in ethyl acetate (50 ml) and washed with water (50 ml), followed by brine (20 ml), dried (MgSO$_4$) and the ethyl acetate evaporated in vacuo. The residue was treated with toluene (20 ml), and the toluene then evaporated in vacuo to give the trimethylsilyl ether of the starting material. The trimethylsilyl ether was taken up in dry dichloromethane (5 ml), treated with N-methylmorpholine (0.30 ml), cooled to −30° and a solution of phosgene in toluene (0.80 ml; 12.5% w/w; 91 mg COCl$_2$), diluted with dry dichloromethane (1 ml) was added dropwise. The mixture was allowed to warm to room temperature to give a solution of the imidoyl chloride, $\nu_{max}$ 1780, 1700 cm$^{-1}$.

A solution of tetramethylguanidinium azide in dichloromethane (0.8 ml 100 mg/ml) was added to the reaction mixture. After 10 min. a further 0.25 ml of the azide solution was added and the mixture stirred for a further 10 mins., The solution was then diluted with dichloromethane (50 ml) and washed with water (50 ml), followed by brine (25 ml). The dichloromethane solution was then dried (MgSO$_4$) and evaporated in vacuo. Toluene was added to the residue and evaporated in vacuo to leave the crude product, e11. The product was chromatographed on silica gel (230-400 mesh ASTM, 18 g), eluting with ethyl acetate. Fractions containing the product were combined and evaporated in vacuo to give e 11 (105 mg). The material was crystallised from ethyl acetate/diethyl ether to give colourless crystals of p-nitrobenzyl (5R, 6S)-3-[(E)-2-(5-methyltetrazol-1-yl)ethenylthio]-6-[(1S)-1-trimethylsilyloxyethyl]-7-oxo-1-azabicyclo[3.2.0]hept-2-ene-2-carboxylate, e11, (76 mg), m.p. 155°-157°, $\nu_{max}$(EtOH) 331 (ε20,155) and 263 (12,655) nm; $\nu_{max}$ (CH$_2$Cl$_2$) 1780, 1700, 1560, 1520, 1345, 1330, 1140, 840 cm$^{-1}$, δ(CDCl$_3$) 0.15 (9H, s), 1.32 (3H, d, J 6 Hz), 2.59 (3H, s), 2.9–3.5 (3H, m), 4.0–4.4 (2H, m), 5.26 and 5.53 (2H, ABq, J ca. 13 Hz), 7.10 (1H, d, J 14 Hz), 7.42 (1H, d, J 14 Hz), 7.66 (2H, d, J 9 Hz), 8.24 (2H, d, J 9 Hz).

EXAMPLE 8

Preparation of (5R, 6S)-3-[(E)-2-(5-Methyltetrazol-1-yl)ethenylthio]-6-[(1S)-1-Hydroxyethyl]-7-oxo-1-azabicyclo[3.2.0]hept-2-ene-2-carboxylic acid

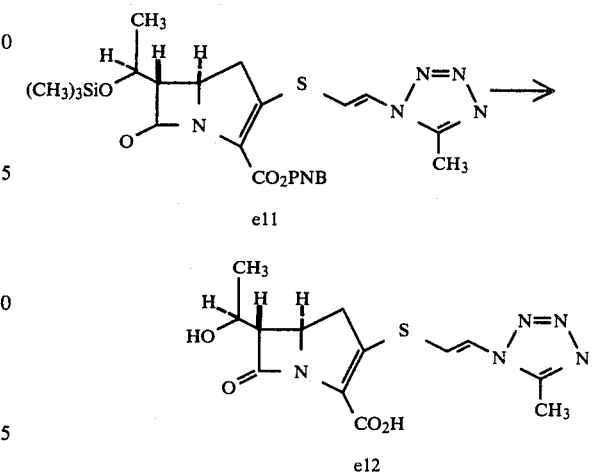

The ester, e11 (55 mg), in dioxan (2 ml) was added to prehydrogenated (15 min) 5% palladium on carbon catalyst (140 mg) in dioxan (10 ml) and aqueous pH 7 0.05 M phosphate buffer solution (5 ml). The mixture was hydrogenated for 2.5 hours and then worked up using a similar procedure to that described in Example 4 to give (5R, 6S)-3-[(E)-2-(5-methyltetrazol-1-yl)ethenylthio]-6-[(1S)-1-hydroxyethyl]-7-oxo-1-azabicyclo[3.2.0]hept-2-ene-2-carboxylic acid, e12, as a freeze dried solid, $\nu_{max}$ 316, $\nu_{max}$ (KBr) 1760, 1600 cm$^{-1}$.

| DEMONSTRATION OF EFFECTIVENESS | | | | |
|---|---|---|---|---|
| | COMPOUND OF EXAMPLE | | | |
| ORGANISM | 2* | 4* | 6+ | 8+ |
| *Citrobacter freundii* E88 | 0.2 | ≦0.2 | 2.5 | 12.5 |
| *Enterobacter cloacae* N1 | 3.1 | ≦0.2 | 5.0 | 12.5 |
| *Escherichia coli* 0111 | ≦0.1 | ≦0.2 | 2.5 | 25 |
| *Escherichia coli* JT 39 | 0.2 | 1.0 | 2.5 | 12.5 |
| *Klebsiella aerogenes* A | 0.2 | ≦0.2 | 2.5 | 1.2 |
| *Proteus mirabilis* C977 | 0.8 | ≦0.2 | 5.0 | 25 |
| *Proteus morganii* I580 | 3.1 | 0.5 | 2.5 | 12.5 |
| *Proteus rettgeri* WM16 | 1.6 | ≦0.2 | 5.0 | 25 |
| *Proteus vulgaris* WO91 | 3.1 | ≦0.2 | 5.0 | 25 |
| *Pseudomonas aeruginosa* A | 25 | 125 | >50 | >50 |
| *Salmonella typhimurium* CT10 | 0.2 | ≦0.2 | 5.0 | 25 |
| *Serratia marcescens* US20 | 6.2 | ≦0.2 | 5.0 | 25 |
| *Shigella sonnei* MB 11967 | 0.2 | ≦0.2 | 2.5 | 12.5 |
| *Bacillus subtilis* A | 0.4 | ≦0.2 | 2.5 | 5.0 |
| *Staphylococcus arreus* Oxford | 0.2 | 0.5 | 1.2 | 0.5 |
| *Staphylococcus aureus* Russell | — | 0.5 | 1.2 | 0.5 |
| *Staphyloccus aureus* 1517 | 0.8 | 2.0 | 12.5 | 12.5 |
| *Streptococcus faecalis* I | 0.8 | 4.0 | >50 | >50 |
| *Streptococcus pneumoniae* CN33 | — | 1.0 | ≦0.1 | ≦0.1 |
| *Streptococcus pyogenes* CN10 | 0.4 | — | — | — |
| *E. coli* ESS | ≦0.1 | ≦0.2 | 0.5 | 0.2 |

*Microtitre using Nutrient broth
+DST agar + 10% horse blood
— inoculum 0.001 ml of a 10$^{-2}$ dilution for G + ve bacteria or a 10$^{-4}$ dilution for G −ve organisms

EXAMPLE 9

Preparation of p-Nitrobenzyl (5R, 6R)-3-[(E)-2-(5-Methyltetrazol-1-yl)ethenylthio]-6-[sodium(1S)-1-sulphonatooxyethyl]-7-oxo-1-azabicyclo[3.2.0]hept-2-ene-2-carboxylate

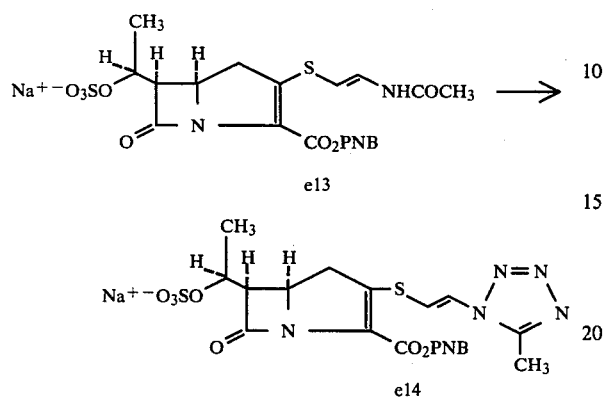

p-Nitrobenzyl (5R, 6R)-3-[(E)-2-acetamidoethenylthio]-6-[sodium(1S)-1-sulphonatooxyethyl]-7-oxo-1-azabicyclo[3.2.0]hept-2-ene-2-carboxylate, e 13, (1.0 g) in water (100 ml) was treated with an aqueous solution of tetra-n-butylammonium hydrogen sulphate (308 mg) which had been neutralised to pH 7 by addition of aqueous tetra-n-butylammonium hydroxide. The mixture was extracted with dichloromethane (4×100 ml), and the extract was dried (MgSO4) and evaporated in vacuo to leave the tetrabutylammonium salt corresponding to e13. This was taken up in dry dichloromethane (15 ml) and treated with N-methylmorpholine (1.5 ml), cooled to −30° and treated with a solution of phosgene in toluene (3.2 ml 12.5% solution; 364 mg COCl2). After warming to ambient, monitoring by infra red (i.r.) spectroscopy suggested some amide was present. N-methylmorpholine (0.5 ml) was added, the solution was cooled and the phosgene solution (1.0 ml) was added. On warming to ambient i.r. indicated complete formation of the imidoyl chloride. Tetramethyl-guanidinium azide (300 mg) in CH2Cl2 (1.5 ml) was added. After 15 min the reaction had not gone to completion so a further aliquot (100 mg) of tetramethyl-guanidinium azide was added. Two further aliquots (each 100 mg) were added and the solution was then diluted with dichloromethane (100 ml) and washed with water (2×100 ml), followed by brine (50 ml). The solution was dried (MgSO4) and evaporated in vacuo. The residue was chromatographed on silica gel (4×10 cm; 1:1 mixture of 200-400 mesh ASTM and finer than 230 mesh ASTM), eluting with dichloromethane (20 ml), followed by chloroform/ethanol (4:1). This gave the tetra-n-butylammonium salt corresponding to e14 (716 mg), $\nu_{max}$. (EtOH) 326, 274 nm, $\nu_{max}$. (CH2Cl2) 1770, 1700 cm$^{-1}$.

The salt was taken up in acetone (5 ml) and treated with sodium iodide (1 equivalent) in acetone (2 ml). After cooling in a refrigerator the sodium salt, e14, was filtered off. The filtrate was rechromatographed on silica gel (14×2.3 cm) eluting with chloroform followed by chloroform/ethanol mixture; 4:1 (50 ml), 7.3 (50 ml) 3:2, to give the sodium salt (134 mg) and a mixture of the sodium and tetra-n-butylammonium salts. Further treatment with NaI and chromatography yielded more sodium salt, e14, (215 mg). The title compound showed the following spectral characteristics;

$\nu_{max}$. (H2O) 325 ($\epsilon_{max}$.14,200) and 272 (11,134) nm; $\nu_{max}$. (KBr) 1780, 1695 cm$^{-1}$; δ[(CD3)2NCDO] inter alia 1.48 (3H, d, J ca 6 Hz), 2.70 (3H, s), 4.1–4.8 (2H, m), 5.36 and 5.50 (2H, ABq, J ca 15 Hz), 7.49 (1H, d, J ca 14 Hz) 7.78 (1H, d, J ca 14 Hz), 7.84 (2H, d, J 9 Hz), 8.27 (2H, d, J 9 Hz) ppm.

EXAMPLE 10

Preparation of Sodium (5R, 6R)-3-[(E)2-(5-Methyltetrazol-1-yl)ethenylthio]-6-[sodium(1S)-1-sulphonatooxyethyl]-7-oxo-1-azabicyclo[3.2.0]hept-2-ene-2-carboxylate

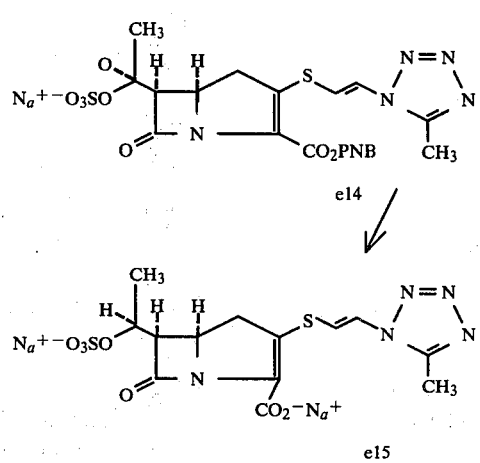

p-Nitrobenzyl (5R, 6R)-3-[(E)2-(5-methyltetrazol-1-yl)ethenylthio]-6-[sodium(1S)-1-sulphonatooxyethyl]-7-oxo-1-azabicyclo[3.2.0]hept-2-ene-2-carboxylate, e14, (354 mg) in water (28 ml) and dioxan (59 ml) was hydrogenated at atmospheric pressure over 5% palladium on carbon catalyst (530 mg) for 2¼ hr. The solution was treated with NaHCO3 (50 mg) and then filtered through Celite. The filter pad was washed with water (100 ml) and the combined filtrate and washings were reduced in volume on a rotary evaporator. The solution was then extracted with ethylacetate (4×200 ml), filtered through Celite and the volume of the aqueous solution was then reduced to ca 20 ml by evaporation in vacuo. The solution was then loaded onto a column of Biogel P-2 (4×20 cm), and the column eluted with water. Fractions with a chromophore at ca 315 nm were combined, evaporated in vacuo to ca 30 ml. and the solution was freeze-dried to give sodium (5R, 6R)-3-[(E)-2-(5-methyltetrazol-1-yl)ethenylthio]-6-[sodium(1S)-1-sulphonatooxyethyl]-7-oxo-1-azabicyclo[3.2.0]hept-2-ene-2-carboxylate, e15 (175 mg). $\nu_{max}$. (H2O) 313 nm ($\epsilon_{max}$.10,130), $\nu_{max}$. (KBr) 1750, 1600, 1400, 1255–1225 cm$^{-1}$. δ(D2O) 1.32 (3H, d, J 6.2 Hz), 2.43 (3H,s), 3.02 (1H, dd, J 17.9 and 9.8 Hz), 3.29 (1H, dd, J 17.7 and 8.9 Hz), 3.71 (1H, dd, J 9.1 and 5.6 Hz) 4.14–4.28 (1H,m), ca 4.65 (1H,m), 7.31 and 7.25 (2H, ABq, J ca 13 Hz) ppm.

EXAMPLE 11

Preparation of p-Nitrobenzyl (5R, 6R)-3-[2-(5-Methyltetrazol-1-yl)ethylthio]-6-[tetra-n-butylammonium(1S)-1-sulphonatooxyethyl]-7-oxo-1-azabicyclo[3.2.0]hept-2-ene-2-carboxylate

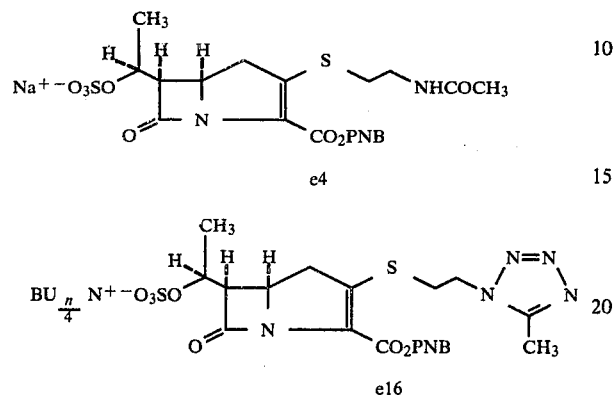

p-Nitrobenzyl (5R, 6R)-3-[(2-acetamidoethylthio)-6-(sodium)(1S)-1-sulphonatooxyethyl]-7-oxo-1-azabicyclo[3.2.0]hept-2-ene-2-carboxylate, e4, (1.1 g) in water (100 ml) was treated with tetra-n-butylammonium sulphate in water (100 ml) [prepared from aqueous Bu(n/4)NHSO$_4$ (340 mg) by neutralisation to pH 7 with aqueous Bu(n/4)NOH] and the resultant mixture was extracted with dichloromethane (4×100 ml). The dichloromethane was dried (MgSO$_4$), evaporated in vacuo and the residue treated with toluene (2×50 ml) which was evaporated in vacuo. Treatment of the residue with anhydrous dichloromethane (50 ml) and rapid evaporation in vacuo gave the tetra-n-butylammonium salt corresponding to e4 as a solid foam (1.3 g), $\nu_{max}$ 315 ($\epsilon_{max}$. 11,515), 266 ($\epsilon_{max}$. 10,785) nm. This was taken up in dry dichloromethane (15 ml) and treated with N-methylmorpholine (1.8 ml), cooled to −30° and treated with phosgene in toluene (3.5 ml, 12.5%, d 0.91 = 398 mg COCl$_2$). On warming to ambient the i.r. spectrum indicated formation of imidoyl chloride. Tetramethylguanidinium azide (350 mg) in dichloromethane (3.5 ml) was added dropwise and after stirring for 20 min the solution was diluted to 100 ml with dichloromethane and washed with water (100 ml). After drying (MgSO$_4$) the dichloromethane was evaporated in vacuo and toluene (2×50 ml) was added to the residue and evaporated in vacuo. Chromatography on silica gel (4.0×15 cm) eluting with CHCl$_3$ (50 ml) followed by chloroform/ethanol mixtures; 9:1 (50 ml), 8:2 gave p-nitrobenzyl (5R, 6R)-3-[2-(5-methyltetrazol-1-yl)ethylthio]-6-[tetra-n-butylammonium(1S)-1-sulphonatooxyethyl]-7-oxo-1-azabicyclo[3.2.0]hept-2-ene-2-carboxylate, e16, (1.1 g); $\nu_{max}$. (EtOH) 312 ($\epsilon_{max}$. 12,375) and 267 ($\epsilon_{max}$. 11,475) nm., $\nu_{max}$. (CH$_2$Cl$_2$) 1775, 1700 cm$^{-1}$, δ(CDCl$_3$) 1.02 (12H, t, J ca 6 Hz), 1.44 (8H, m), 1.55–1.75 (11H,m), 2.66 (3H,s), 3.05–3.55 (11H, m), 3.75 (1H, dd, J 6 and 10.5 Hz), 4.20 (1H, dd J 8 and 19 Hz), 4.39 (1H, m), 4.5–4.63 (1H,m), 4.64–4.8 (2H,m), 5.24 (1H,d,J ca 13 Hz), 5.48 (1H,d,J ca 13 Hz), 7.64 (2H,d, J ca 9 Hz), 8.23 (2H, d,J 9 Hz) ppm.

EXAMPLE 12

Preparation of Sodium (5R, 6R)-3-[2-(5-Methyltetrazol-1-yl)ethylthio]-6-[sodium(1S)-1-sulphonatooxyethyl]-7-oxo-1-azabicyclo[3.2.0]hept-2-ene-2-carboxylate

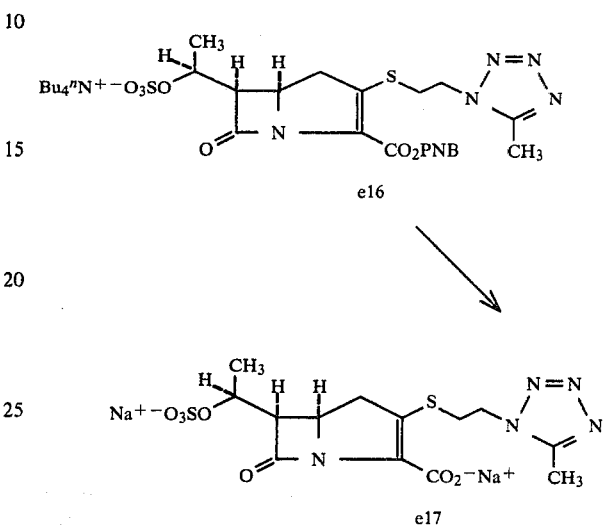

p-Nitrobenzyl (5R, 6R)-3-[2-(5-methyltetrazol-1-yl)ethylthio]-6-[tetra-n-butylammonium(1S)-1-sulphonatooxyethyl]-7-oxo-1-azabicyclo[3.2.0]hept-2-ene-2-carboxylate, e16, (1.2 g) in dioxan (150 ml) and water (75 ml) was hydrogenated over 5% Pd/c catalyst (1.5 g) for 3.25 hr. Sodium hydrogen carbonate (140 mg) was added, the catalyst filtered off on Celite, and washed thoroughly with water (300 ml). The volume of combined filtrate and washings was reduced to ca 300 ml, sodium tetrafluoroborate (200 mg) was added and the solution extracted with ethyl acetate (4×500 ml), followed by dichloromethane (500 ml). The aqueous solution was reduced to ca 200 ml by evaporation in vacuo, treated with NaCl (10 g) and loaded onto a column of DIAION HP-20 (4×16 cm). The column was eluted with 5% aqueous NaCl (100 ml) followed by H$_2$O. Fractions were monitored by u.v. Those with an absorption at ca 296 nm were combined, reduced in volume to ca 100 ml and freeze-dried to give sodium (5R, 6R)-3-[2-(5-methyltetrazol-1-yl)ethylthio]-6-[sodium(1S)-1-sulphonatooxyethyl]-7-oxo-1-azabicyclo[3.2.0]hept-2-ene-2-carboxylate, e17, (320 mg), as a colourless solid, $\nu_{max}$. (H$_2$O) 296 ($\epsilon_{max}$. 7,418) nm., $\nu_{max}$. (KBr) 1755, 1600, 1405, 1225 cm$^{-1}$, δ(D$_2$O) 1.31 (3H, d, J 6.5 Hz), 2.39 (3H,s), 2.70 (1H, dd, J 9.8 and 18.0 Hz), 3.00 (1H, dd, J 9.1 and 18.0 Hz), 3.06–3.35 (2H,m), 3.65 (1H, dd, J 5.5 and 9 Hz), 3.9–4.1 (1H,m), 4.36–4.6 (m) ppm.

EXAMPLE 13

Preparation of Sodium (5R, 6R)-6-[(1S)-1-Hydroxyethyl]-3-[2-(5-methyltetrazol-1-yl)ethylthio]-7-oxo-1-azabicyclo[3.2.0]hept-2-ene-2-carboxylate

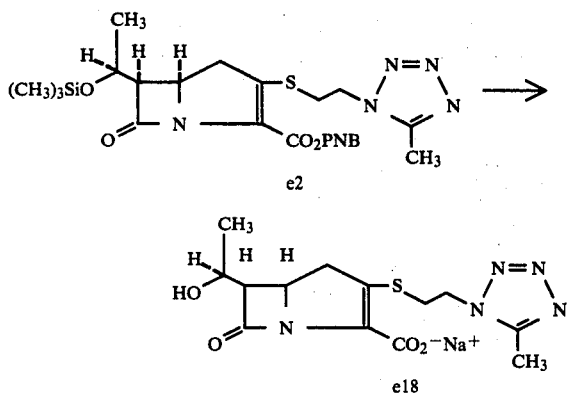

The ester, e2, (563 mg) in dioxan (90 ml) and water (45 ml) was hydrogenated over 5% Pd/C catalyst (760 mg) for 2.5 hr. Sodium hydrogen carbonate (87 mg) in water (5 ml) was added and the mixture was filtered through Celite. The filter cake was washed with water (300 ml) and the combined filtrate and washings were reduced in volume to ca 150 ml by evaporation in vacuo. The solution was then washed with ethyl acetate (4×150 ml), the aqueous layer was again filtered through Celite, evaporated in vacuo to ca 15 ml and chromatographed on a Biogel P-2 column (4×19 cm), eluting with water. Relevant fractions ($\lambda_{max}$. 297) were combined and evaporated in vacuo to ca 50 ml and freeze-dried to give the sodium salt, e18, (263 mg), $\lambda_{max}$. (H$_2$O) 296 nm, $\nu_{max}$. (KBr) 1750, 1590, 1400 cm$^{-1}$, δ (D$_2$O) 1.13 (3H, d J 6.2 Hz), 2.39 (3H, s), 2.65 (1H, dd, J 17.6 and 9.7 Hz), 2.77 (1H, dd, J 17.5 and 9.4 Hz), 2.8–3.16 (1H,m), 3.24–3.36 (1H,m), 3.41 (1H, dd, J 9.8 and 5.4 Hz), 3.80–3.95 (2H,m), 4.4–4.55 (2H,m) ppm.

EXAMPLE 14

(i) Preparation of 2-(5-Methyltetrazol-1-yl)ethylthiol

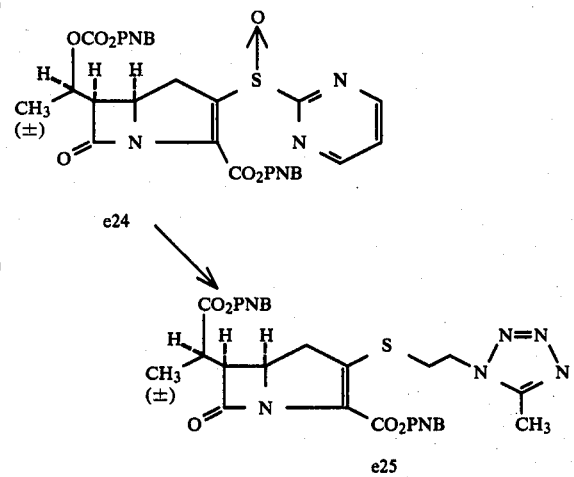

N,S-Diacetyl β-mercaptoethylamine, e21, (805 mg) in dichloromethane (16 ml) was treated with N-methylmorpholine (3.3 ml). The reaction mixture was cooled to −40° and treated with phosgene (8.7 ml, 12.5% solution in toluene, d. 0.91; 990 mg COCl$_2$). After warming to room temperature tetramethylguanidinium azide (1.0 g) in dichloromethane (10 ml) was added. After stirring for 15 min. the reaction mixture was washed with water (2×20 ml), dried (MgSO$_4$) and evaporated in vacuo. Toluene was added to the residue and evaporated in vacuo to remove residual N-methylmorpholine. The crude product was chromatographed on silica gel (230–400 mesh ASTM, 2.5×12 cm column) eluting with ethyl acetate to give 2-(5-methyltetrazol-1-yl)ethylthioacetate, e22, (767 mg), $\nu_{max}$. (CH$_2$Cl$_2$) 1795, 1530, 1410, 1360, 1135, 1110, 1080 and 940 cm$^{-1}$, δ(CDCl$_3$) 2.30 (3H,s), 2.68 (3H,s), 3.40 (2H, t, J ca 7.5 Hz), 4.54 (2H, t, J ca 7.5 Hz). 2-(5-methyltetrazol-1-yl)ethyl thioacetate, e22, (100 mg) was suspended in 0.1 M aqueous NaOH (11 ml) and the mixture was stirred vigorously under argon at room temperature. After ca 15 min. the oil seemed to have dissolved. After 30 min. the solution was neutralised to pH 7 by addition of dilute HCl. The solution was then extracted with ethyl acetate (2×20 ml) and the extract dried (MgSO$_4$) and evaporated in vacuo. Toluene (20 ml) was added and evaporated in vacuo. The residue was taken up in dichloromethane (20 ml). Evaporation in vacuo left the thiol, e23, as an oil (31 mg), $\nu_{max}$. (CH$_2$Cl$_2$) 3050, 2950, 2850 (broad), 1530, 1410, 1320, 1110, 1085 cm$^{-1}$, δ(CDCl$_3$) 1.51 (1H, broad s), 2.65 (3H,s), 3.12 (2H, broad t, J ca 6 Hz), 4.51 (2H, t, J 6.5 Hz) ppm. Found M+ m/e 144.046 7; C$_4$H$_8$N$_4$S requires m/e 144.046 9.

(ii) Preparation of p-Nitrobenzyl (5RS, 6SR)-6-[(1RS)-1-p-Nitrobenzyloxycarbonyloxyethyl]-3-[2-(5-methyltetrazol-1-yl)ethylthio]-7-oxo-1-azabicyclo[3.2.0]hept-2-ene-2-carboxylate p-Nitrobenzyl (5RS, 6SR)-6-[(1RS)-1-p-nitrobenzyloxycarbonyloxyethyl]-3-(2-pyrimidylsulphinyl)-7-oxo-1-azabicyclo[3.2.0]hept-2-ene-2-carboxylate (136 mg) in dichloromethane (5 ml) was cooled in an ice-bath, treated with benzyldimethyl-n-hexadecylammonium chloride (4 mg) followed by 2-(5-methyltetrazol-1-yl)ethylthiol (29 mg), followed by 0.1 M aqueous sodium hydroxide (2.1 ml). The mixture was stirred vigourously for 45 min, then allowed to warm to room temperature and stirred for a further 15 min. The mixture was diluted with dichloromethane (25 ml) and brine (25 ml). After separation the dichloromethane layer was dried (MgSO$_4$) and evaporated in vacuo. Chromatography on silica gel (2.5×12 cm., 230–400 mesh ASTM) eluting with ethyl acetate (200 ml) followed by ethyl acetate/ethanol (95:5) gave the title compound, e25, (64 mg), $\nu_{max}$. (CH$_2$Cl$_2$) 1790, 1755, 1710 and 1610 cm$^{-1}$. δ (CDCl$_3$) 1.48 (3H, d, J ca 6.5 Hz), 2.56 (3H,s), 2.83 (1H, dd, J 8 and 18 Hz), 3.06 (1H, dd, J 10 and 18 Hz), 3.25–3.52 (3H, m), 4.12 (1H, approx d t, J 2.5 and 10 Hz), 4.38–4.62 (2H, m), 5.05–5.20 (1H,m), 5.23 (1H,d, J 13 Hz), 5.28 (2H,s), 5.47 (1H, d, J 13 Hz), 7.58 (2H, d, J 9 Hz), 7.62 (2H, d, J 9 Hz), 8.23 (2H, d, J 9 Hz), 8.26 (2H, d, J 9 Hz) ppm.

EXAMPLE 15

Preparation of sodium (5RS, 6SR)-6-[(1RS)-1-Hydroxyethyl]-1-[2-(5-methyltetrazol-1-yl)ethylthio]-7-oxo-1-azabicyclo[3.2.0]hept-2-ene-2-carboxylate

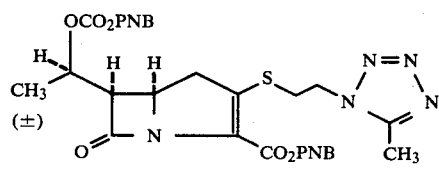

e25

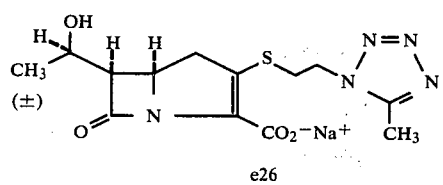

e26

The ester, e25, (70 mg) in dioxan (12 ml) and water (6 ml) was hydrogenated over 5% Pd/C catalyst (120 mg) for 2.25 hr. Sodium hydrogen carbonate (9 mg) in water (2 ml) was added and the mixture was then filtered through Celite. The filter cake was washed with water (70 ml) and the combined filtrate and washings were evaporated in vacuo to ca 50 ml. The solution was then washed with ethyl acetate (3×150 ml), and then reduced in volume to ca 10 ml by evaporation in vacuo. The solution was loaded onto a column of DIAION HP-20 (2.5×10 cm) and the column eluted with water (300 ml), followed by water/ethanol mixtures; 95:5 (100 ml); 90:10 (100 ml).

The fractions were monitored by u.v. spectroscopy, fractions containing a maximum at ca 298 nm were combined, evaporated in vacuo to ca 10 ml and freeze-dried to give the title compound, e26, as a solid (20 mg), $\lambda_{max}$. (H$_2$O) 298 ($\epsilon_{max}$. 7712) nm., $\lambda_{max}$. (KBr) 1750, 1595, 1400 cm$^{-1}$. $\delta$ (D$_2$O) 1.26 (3H,d,J 6 Hz), 2.58 (3H,s), 2.83 (1H, dd, J 9.5 and 18 Hz), 2.98 (1H, dd, J 10.5 and 18 Hz), 3.2–3.35 (2H, dd, J 3 and 6 Hz at $\delta$ 3.20 ppm superimposed on m), 3.38–3.50 (1H,m), 3.99 (1H, dt, J 3 and 10 Hz), 4.19 (1H, quintet, J 6 Hz), 4.57–4.75 (2H, m) ppm.

EXAMPLE 16

Preparation of p-Nitrobenzyl (5R, 6R)-3-[(E)-2-(5-Methyltetrazol-1-yl)ethenylthio]-6-[(1S)-1-trimethylsilyloxyethyl]-7-oxo-1-azabicyclo[3.2.0]hept-2-ene-2-carboxylate and p-Nitrobenzyl (5R, 6R)-6-[(1S)-1-Hydroxyethyl-3-[(E)-2-(5methyltetrazol-1-yl)ethenylthio]-7-oxo-1-azabicyclo[3.2.0]hept-2-ene-2-carboxylate

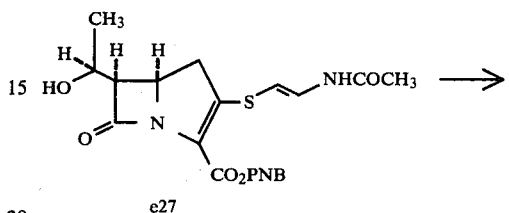

e27

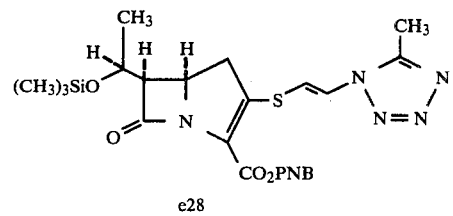

e28

+

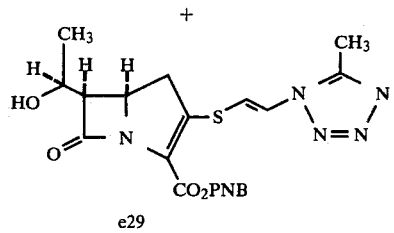

e29 p-Nitrobenzyl (5R, 6R)-3-[(E)-2-acetamidoethenylthio]-6-[(1S)-1-hydroxyethyl]-7-oxo-1-azabicyclo[3.2.0-]hept-2-ene-2-carboxylate (e27) (200 mg) in pyridine (5 ml) was treated with chlorotrimethylsilane (360 mg). After 15 min. the solvent and excess chlorotrimethylsilane were removed by evaporation in vacuo. Ethyl acetate (50 ml) was added to the residue and then washed with water (2×20 ml), followed by brine (20 ml). After drying the ethylacetate was evaporated in vacuo, toluene was added to the residue and evaporated in vacuo to leave the silyl ether corresponding to the starting material. This was taken up in dry dichloromethane (5 ml) and N-methylmorpholine (0.25 ml) was added. The reaction mixture was cooled to −30° and phosgene in toluene (0.63 ml, 12.5% w/w d. 0.91), diluted with dichloromethane (2 ml), was added. The reaction mixture was allowed to warm to room temperature when the infra red spectrum indicated formation of the imidoyl chloride. Tetramethylguanidinium azide (70 mg) in dichloromethane (0.7 ml) was added. After 15 min t.l.c. indicated incomplete formation of the tetrazole so more azide (30 mg) in dichloromethane (0.3 ml) was added, and after 5 min the reaction mixture was worked up by dilution with dichloromethane (30 ml) followed by washing with water (20 ml) and then with brine (20 ml). After drying (MgSO$_4$) the dichloromethane was evaporated in vacuo, toluene (20 ml) was added and evaporated in vacuo. After keeping for 16 hr. at 4° the product was chromatographed on a silica gel column (230–400 mesh ASTM, 2.5×10 cm) eluting with ethyl acetate/hexane mixtures; 7:3 (100 ml), 8:2 (100 ml), then with ethyl acetate (100 ml) followed by ethyl acetate/ethanol mixtures; 9:1 (100 ml), 8:2. Fractions were monitored by t.l.c. Those containing the silyl ether of the product were combined, evaporated in vacuo. The resultant oil (67 mg) crystallised on standing. Recrystallisation from ethyl acetate/hexane gave p-nitrobenzyl (5R, 6R)-3-[(E)-2-(5-methyltetrazol-1-yl)ethenylthio]-6-[(1S)-1-trimethylsilyloxyethyl]-7-oxo-1-azabicyclo[3.2.0]hept-2-ene-2-carboxylate (e28) (53 mg) mp. 154°–156°, $\nu_{max}$. (CH$_2$Cl$_2$) 1790, 1705, 1630, 1610, 1570, 1525, 1350, 1335, 1040, 850 cm$^{-1}$. $\lambda_{max}$. (EtOH) 328 ($\epsilon_{max}$. 21,705) and 262 ($\epsilon$ 13,724) nm, $\delta$(CDCl$_3$) 0.10 (9H,s), 1.34 (3H,d, J ca 6 Hz), 2.63 (3H,s), 3.12 (1H,dd, J 10 and 18 Hz), 3.64 (1H, approx t, J ca 5.5 Hz), 3.90 (1H, dd, J 8 and 18 Hz), 4.3–4.45 (2H, m), 5.30 (1H, d, J ca 14 Hz), 5.53 (1H, d, J ca 14 Hz), 7.11 (1H, d, J ca 14 Hz), 7.44 (1H, d, J ca 14 Hz), 7.77 (2H, d, J ca 9 Hz), 8.24 (2H, d, J ca 9 Hz) ppm.

Later fractions gave p-nitrobenzyl (5R, 6R)-6-[(1S)-1-hydroxyethyl]-3-[(E)-2-(5-methyltetrazol-1-yl)ethenylthio]-7-oxo-1-azabicyclo[3.2.0]hept-2-ene-2-carboxylate (e29) which crystallised ex CHCl$_3$/EtOH to give crystals (24 mg) m.p. 175°, $\lambda_{max}$. (EtOH) 326 ($\epsilon_{max}$. 19,261) and 264 ($\epsilon$ 13,442) nm., $\nu_{max}$. (KBr) 1750, 1695, 1625, 1605, 1560, 1518, 1350, 1330 cm$^{-1}$, $\epsilon$[(CD$_3$)$_2$ NCDO] 1.32 (3H, d, J ca 6 Hz), 2.74 (3H,s), 3.49 (1H, dd, J 10 and 18 Hz), 3.71 (1H, dd, J 6 and 9 Hz), 3.71 (1H, dd, J 8.5 and 18 Hz), 4.10–4.25 (1H, m), 4.35–4.38 (1H,m), 5.19 (1H,d,J ca 6 Hz), 5.44 (1H,d,J ca 14 Hz), 5.63 (1H,d, J ca 14 Hz), 7.64 (1H, d, J ca 14 Hz), 7.86 (1H, d, J ca 14 Hz), 7.87 (2H, d, J ca 9 Hz), 8.32 (2H, d, J ca 9 Hz) ppm.

EXAMPLE 17

Preparation of Sodium (5R, 6R)-6-[(1S)-1-Hydroxyethyl]-3-[(E)-2-(5-methyltetrazol-1-yl)ethenylthio]-7-oxo-1-azabicyclo[3.2.0]hept-2-ene-2-carboxylate

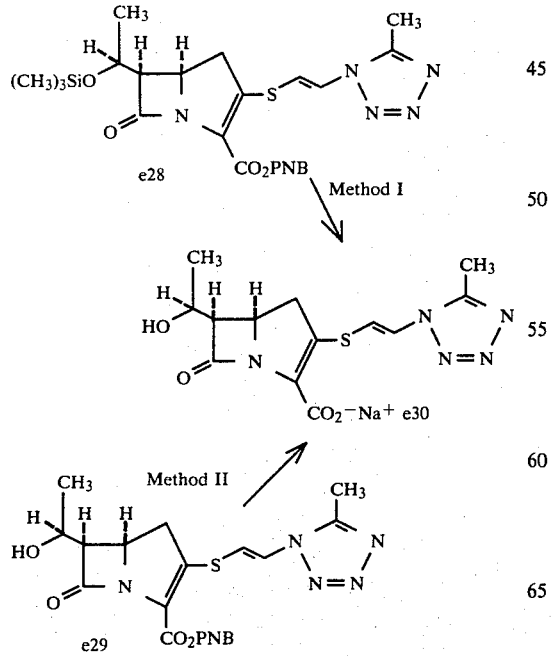

Method I p-Nitrobenzyl (5R, 6R)-3-[(E)-2-(5-methyltetrazol-1-yl)ethenylthio]-6-[(1S)-1-trimethylsilyloxyethyl]-7-oxo-1-azabicyclo[3.2.0]hept-2-ene-2-carboxylate (e28) (60 mg) in dioxan (12 ml) and water (6 ml) was hydrogenated at atmospheric pressure for 2½ hour over 5% Pd/C catalyst (80 mg). Sodium hydrogen carbonate (9.1 mg) was than added in H$_2$O (20 ml). Mixture was then filtered through Celite and the filter cake washed with water (10 ml). The volume of combined filtrate and washings was reduced to ca 30 ml by evaporation in vacuo and the solution was then washed with ethyl acetate (3×50 ml). This provided an aqueous solution of the sodium salt (e30). After evaporation in vacuo to a small volume the solution was freeze-dried to give sodium (5R, 6R)-6-[(1S)-1-hydroxyethyl]-3-[(E)-2-(5-methyltetrazol-1-yl)ethenylthio]-7-oxo-1-azabicyclo[3.2.0]hept-2-ene-2-carboxylate (e30), $\lambda_{max}$. (H$_2$O) 315 n.m., $\nu_{max}$. (KBr) 1750, 1590, 1400 cm$^{-1}$, $\delta$ (D$_2$O) 1.33 (3H,d, J ca 6 Hz), 2.60 (3H,s), 3.21 (1H, dd, J 10 and 19 Hz), 3.36 (1H, dd, J 9 and 19 Hz), 3.66 (1H, dd, J 5.5 and 9 Hz), 4.10–4.25 (1H,m), 4.28–4.30 (1H, m), 7.42 (1H, d, J ca 14 Hz), 7.49 (1H, d, J ca 14 Hz).

Method II p-Nitrobenzyl (5R, 6R)-6-[(1S)-1-hydroxyethyl]-3-[(E)-2-(5-methyl-1-tetrazol-1-yl)ethenylthio]-7-oxo-1-azabicyclo[3.2.0]hept-2-ene-2-carboxylate (18 mg) in dioxan (6 ml) and water (3 ml) containing 5% Pd/C catalyst (25 mg) was hydrogenated and worked up in an analogous way to that described in Method I to give the sodium salt, e30, $\lambda_{max}$. (H$_2$O) 315 n.m.

EXAMPLE 18

Preparation of Phthalidyl (5R, 6R)-3-[2-(5-methyltetrazol-1-yl)ethylthio]-6-[(1S)-1-trimethylsilyloxyethyl]-7-oxo-1-azabicyclo[3.2.0]hept-2-ene-2-carboxylate

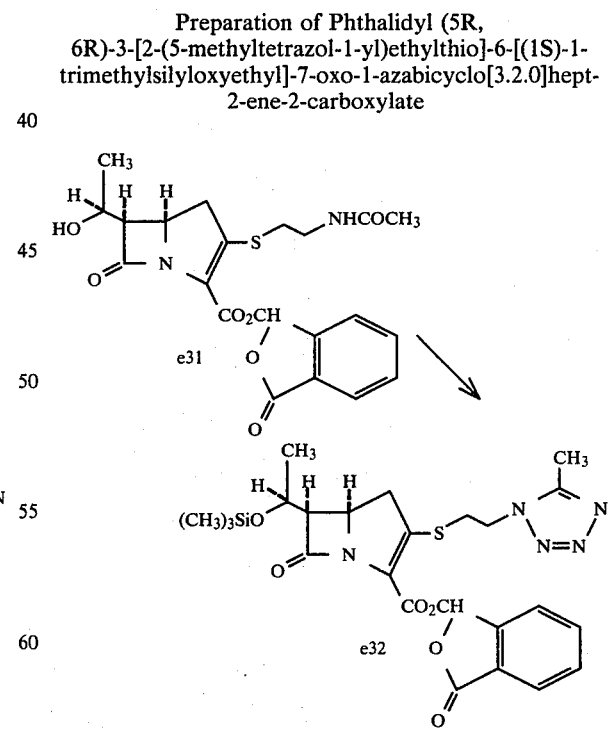

A crystalline sample of phthalidyl (5R, 6R)-3-(2-acetamidoethylthio)-6-[(1S)-1-hydroxyethyl]-7-oxo-1-azabicyclo[3.2.0]hept-2-ene-2-carboxylate (446 mg) in pyridine (6 ml) was treated with chlorotrimethylsilane (800 mg). After 1 hr. excess pyridine and chlorotrimethylsilane were removed by evaporation in vacuo. The residue was taken up in ethyl acetate (30 ml), washed with water (30 ml), brine (30 ml) and then dried (MgSO₄) and evaporated in vacuo. Toluene (30 ml) was added to the residue and evaporated in vacuo to give the silyl ether corresponding to the starting material. This was taken up in dichloromethane (12 ml) and treated with N-methylmorpholine (0.8 ml). The mixture was cooled to $-30°$ and treated with phosgene in toluene (1.72 ml 12.5% w/w d 0.91). On warming to room temperature i.r. indicated the formation of the imidoyl chloride. The solution was then treated with tetramethylguanidinium azide in dichloromethane (1.9 ml 100 mg/ml). After 15 min t.l.c. indicated incomplete reaction so a further 0.3 ml of the solution of azide was added. After 3 minutes the solution was washed with water (2×30 ml), followed by brine (20 ml), dried (MgSO₄) and evaporated in vacuo. Toluene (100 ml) was added and evaporated in vacuo to give the crude product (502 mg). Addition of warm ethylacetate caused crystallisation to give the product e32, as a colourless crystalline solid (310 mg), m.p. 203°–205° (decomp), $\nu_{max.}$ (CH₂Cl₂) 1790, 1710, 1130, 975, 845 cm⁻¹, $\lambda_{max.}$ (EtOH) 320 ($\epsilon_{max.}$ 11,559) and 228 ($\epsilon_{max.}$ 11,727) n.m.

EXAMPLE 19

Preparation of Phthalidyl (5R, 6R)-6-[(1S)-1-Hydroxyethyl]3-[2-(5-methyltetrazol-1-yl)ethylthio]-7-oxo-1-azabicyclo[3.2.0]hept-2-ene-2-carboxylate

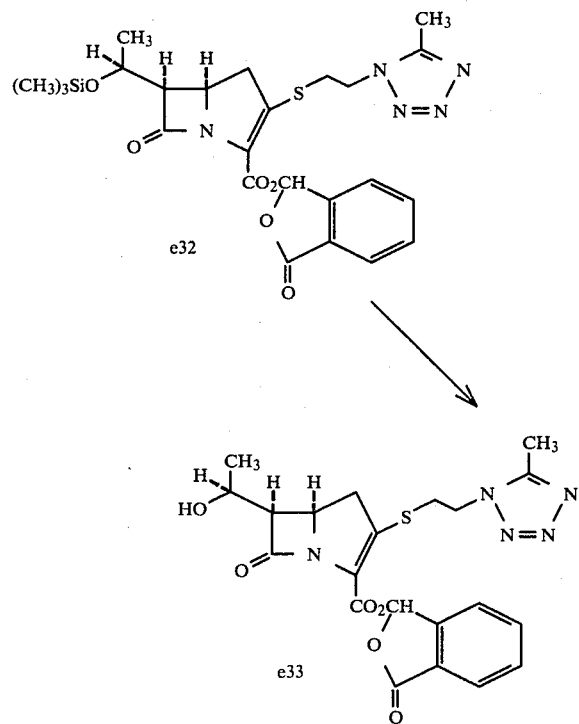

The silylether, e32, (190 mg) in tetrahydrofuran (15 ml) was treated with 0.05 M HCl (0.5 ml). After ca 15 minutes t.l.c. indicated that most of the silyl ether had been cleaved. Ethyl acetate (50 ml) and saturated aqueous sodium hydrogen carbonate (5 ml) were added, followed by saturated brine (30 ml). After shaking and separation the organic layer was dried (MgSO₄) and evaporated in vacuo. The residue was taken up in dichloromethane (10 ml), evaporated in vacuo and then ethyl acetate (5 ml) was added. On warming gently the product crystallised to give the hydroxy compound, e33, (115 mg) m.p. 175°–177°, $\nu_{max.}$ (CH₂Cl₂) 3670, 3580, 1790, 1730, 975 cm⁻¹.

EXAMPLE 20

(i) Preparation of 1-(2-Acetylthioethyl)-5-Triphenylmethylaminomethyltetrazole

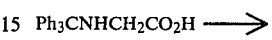

e34

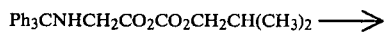

e35

e36

e37

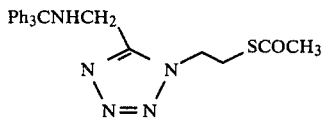

e38

N-Triethylglycine (e34) (1.06 g) was suspended in dichloromethane (25 ml) and treated with triethylamine (0.463 ml) followed by isobutylchloroformate (458 mg). After stirring for 1 hr. the solution of the mixed anhydride, e35, was added to a suspension of 2-aminoethanethiol hydrochloride (379 mg) under argon which had been treated with triethylamine (0.463 ml). Pyridine (0.1 ml) was then added to the mixture. After 4 hr. triethylamine (0.463 ml), followed by acetyl chloride (0.237 ml) were added. After stirring for 1 hr. the solution was washed with water and evaporated to leave an oil which still contained a substantial quantity of thiol e36. This was taken up in tetrahydrofuran (5 ml) and treated with sodium hydride (160 mg, 50% dispersion in oil) followed by acetyl chloride (0.237 ml). After stirring under argon for 1 hr. ethyl acetate (30 ml) was added followed by brine (20 ml). The ethyl acetate layer was dried and evaporated and the residue chromatographed on silica gel (230–400 mesh ASTM, 3×15 cm) eluting with ethyl acetate/hexane mixtures 3:7 (100 ml), 4:6 (300 ml), 1:1 this eventually gave two u.v. positive products, the second of which proved to be the thioacetate, e37, (567 mg), $\nu_{max.}$ (CHCl₃) 3375, 1680 cm⁻¹, δ (CDCl₃) 2.38 (3H,s), 2.54 (1H, s, exch D₂O), 2.99 (2H,s), 3.10 (2H, t, J ca 6 Hz), 3.3–3.6 (2H,m), 7.0–8.0 (16H,m).

The thioacetate, e38, (560 mg) in dichloromethane (10 ml) was treated with N-methylmorpholine (1.0 ml), cooled to $-30°$ and then a solution of phosgene in toluene (2.5 ml, 12.5% w/w d 0.91), diluted with dichloromethane (7.5 ml) was added dropwise. The reaction was then allowed to warm to room temperature and stirred for 15 min. Tetramethylguanadinium azide in solution in dichloromethane (2.2 ml., 100 mg/ml) was then added and stirring was continued for 20 min. More of the solution of azide (0.7 ml) was added and after 3 min. the solution was extracted with water (2×50 ml), dried (MgSO$_4$) and evaporated in vacuo. The mixture was taken up in dichloromethane (20 ml), loaded onto a column of silica gel (230–400 mesh ASTM, 2.5×20 cm) and the column was eluted with ethyl acetate/hexane 4:6.

1-(2-Acetylthioethyl)-5-triphenylmethylaminomethyltetrazole was obtained, after evaporation in vacuo of relevant fractions, as a foam (298 mg), $\nu_{max}$. (CH$_2$Cl$_2$) 3325 (broad), 1695 cm$^{-1}$. δ (CDCl$_3$) 2.21 (3H, s), 2.60 (1H, broad t, exch. D$_2$O) 3.28 (2H,t, J 7 Hz), 3.60 (2H, d, J 7 Hz, s on D$_2$O exch.), 4.35 (2H,t, J 7 Hz), 7.0–7.8 (15 H,m).

(ii) Preparation of
1-(2-Acetylthioethyl)-5-p-nitrobenzyloxycarbonylaminomethyltetrazole

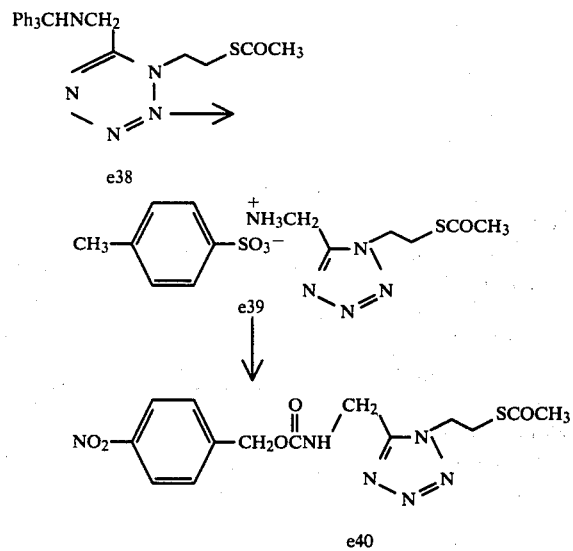

1-(2-Acetylthioethyl)-5-triphenylmethylaminomethyltetrazole, e38, (300 mg) in acetone (3 ml) was cooled to −20° and treated with p-toluenesulphonic acid monohydrate (128 mg) in acetone (2 ml). The reaction mixture was allowed to warm to room temperature and stirred for 7 hours. The resultant colourless solid was filtered off to give the p-toluenesulphonic acid salt, e39, (190 mg), m.p. 184°–185°, $\nu_{max}$ (KBr) 1680, 1235, 1225, 1170, 1150, 1130, 1042, 1015, 838, 688, 572 cm$^{-1}$, (D$_2$O) 2.28 (3H,s), 2.35 (3H,s), 3.34 (2H, t, J Ca 6 Hz), 7.30 (2H, d, J 9 Hz), 7.65 (2H, d, J 9 Hz) ppm. Other signals were obscured by the HOD signal.

The salt, e39, was suspended in dry CH$_2$Cl$_2$ (4 ml) at 0° and treated with p-nitrobenzylchloroformate (100 mg) in CH$_2$Cl$_2$ (1 ml), followed by triethylamine (0.128 ml). After 30 minutes further quantities of p-nitrobenzylchloroformate (20 mg) and triethylamine (0.025 ml) were added and stirring was continued for a further 30 minutes. The solution was then diluted with dichloromethane (20 ml) washed with water (10 ml), dried (MgSO$_4$) and evaporated. The crude product was chromatographed on silica gel (2.5×12 cm, 230–400 mesh ASTM) eluting with ethyl acetate/hexane mixtures; 4:6 (50 ml), 1:1 (50 ml), 6:4 (50 ml), 7:3 (50 ml) and then with ethyl acetate. Fractions containing the desired product were combined and evaporated to give 1-(2-acetylthioethyl)-5-p-nitrobenzyloxycarbonylaminomethyltetrazole (160 mg)$\nu_{max}$ (CH$_2$Cl$_2$) 3430, 1730, 1690, 1520, 1350 cm$^{-1}$, δ(CDCl$_3$) 2.33 (3H,s), 3.34 (2H, t, J Ca 6.5 Hz), 4.58 (2H, t, J Ca 6.5 Hz), 4.74 (2H, d, J 6 Hz), 5.20 (2H,s) 6.66 (1H, t, J Ca 6 Hz), 7.46 (2H, d), 8.14 (2H,d) ppm.

(iii) Preparation of p-Nitrobenzyl (5RS 6SR)-[2-(5-p-Nitrobenzyloxycarbonylaminomethyltetrazol-1-yl)ethylthio]-6-[(1RS)-1-nitrobenzyloxycarbonyloxyethyl]-7-oxo-1-azabicyclo[3.2.0]hept-2-ene-2-carboxylate

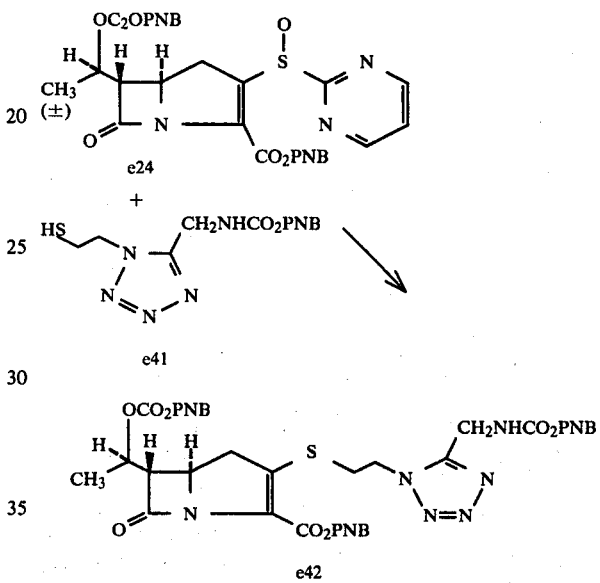

1-(2-Acetylthioethyl)-5-p-Nitrobenzyloxycarbonylaminomethyltetrazole, e40, (100 mg) in dioxan (0.5 ml) was treated with 0.1 N NaOH (5.3 ml). After stirring under argon for 20 minutes the reaction mixture was neutralised to pH7 by addition of dilute aqueous HCl. The mixture was diluted with H$_2$O (50 ml) and ethyl acetate (50 ml), after shaking and separation the ethyl acetate was dried (MgSO$_4$) and evaporated to give the thiol, e41, $\nu_{max}$ (CH$_2$Cl$_2$) 3430, 1730, 1520, 1350, 1235 cm$^{-1}$. The thiol and the sulphoxide, e24, (170 mg) were dissolved in dichloromethane (20 ml) at 0° and treated with 0.1 N NaOH (2.6 ml) and water (5 ml) followed by benzyldimethyl-n-hexadecylammonium chloride (4 mg). After 1 hour at 0° a further 6 mg of the ammonium chloride was added, followed by 0.1 N NaOH (1 ml). After 5 minutes the solution was diluted with H$_2$O (20 ml) and dichloromethane (50 ml). The layers were separated and the dichloromethane layer was dried (MgSO$_4$) and evaporated in vacuo. Chromatography of the crude product on silica gel (230–400 mesh ASTM, 2.5×10 cm) eluting with ethyl acetate gave, after combination and evaporation in vacuo of the relevant fractions, the title compound, e42, (67 mg) $\nu_{max}$(CH$_2$Cl$_2$) 3430, 1790, 1750 (sh), 1730, 1525, 1350 cm$^{-1}$.

EXAMPLE 21

Preparation of 5, 6(SR)-3-[2-(5-aminomethyltetrazol-1-yl)ethyl thio]-6-[1(RS)-1-hydroxyethyl thio]-7-oxo-1-azabicyclo[3,2,0]hept-2-ene-2-carboxylate

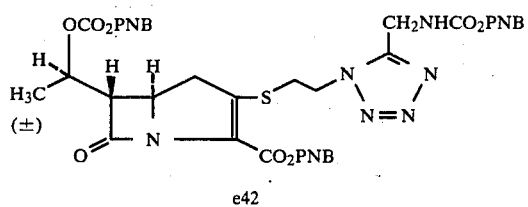

e42

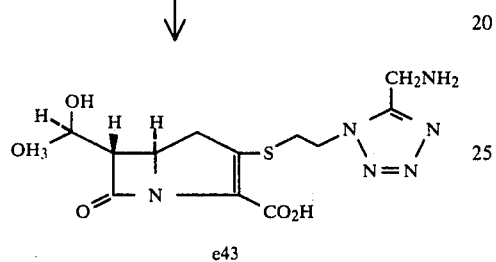

e43 p-Nitrobenzyl (5RS,6SR)-3-[2-(5-p-Nitrobenzyloxycarbonylaminomethyltetrazol-1-yl)ethyl thio]-6-[(1RS)-1-p-nitrobenzyloxycarbonyloxyethyl]-7-oxo-1-azabicyclo[3.2.0]hept-2-ene-2-carboxylate, e42, (58 mg) in dioxan (32 ml) and water (8 ml) was hydrogenated at atmospheric pressure for 2 hours over 10% Pd/C catalyst (100 mg) in the presence of (M/20) phosphate buffer (4 ml). The mixture was then filtered through Celite and the filter cake washed with water (10 ml). The volume of combined filtrate and washings was reduced to ca 18 ml in vacuo and the solution was washed with ethyl acetate (3×20 ml). This provided an aqueous solution of the zwitterion (c43). After evaporation in vacuo to a small volume the solution was freeze-dried to give (5RS, 6SR)-3-[2-(5-aminomethyl tetrazol-1-yl)ethyl thio]-6-[1(RS)-1-hydroxyethylthio]-7-oxo-1-azabicyclo[3.2.0]hept-2-ene-2-carboxylate (e43) λmax (H$_2$O) 297 nm.

EXAMPLE 22

(i) Preparation of (Z)-1-(5-Methyltetrazol-1-yl)-2-triphenylmethylthioethene

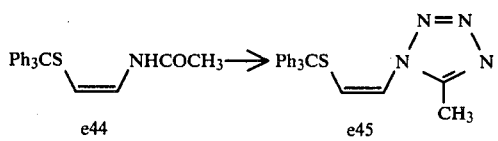

(Z)-1-Acetamido-2-triphenylmethylthioethene, e44, (1.07 g) in dry dichloromethane (30 ml) containing N-methylmorpholine (3.5 ml, 3.22 g) was cooled to −30° and treated with phosgene in toluene (8.4 ml, 12.5% w/w). After warming to room temperature and stirring for 30 minutes tetramethylguanidinium azide (600 mg) in dichloromethane (6 ml) was added. After 45 min. a further quantity of tetramethylguanidinium azide (300 mg) in dichloromethane was added. After a further 45 min. the reaction mixture was warmed with water (2×300 ml), followed by saturated brine. After drying (MgSO$_4$) the dichloromethane was evaporated in vacuo. Toluene (30 ml) was added and evaporated in vacuo (2×) and the residual material was crystallised from ethyl acetate/hexane to give (Z)-1-(5-methyltetrazol-1-yl)-2-triphenylmethylthioethene (827 mg), m.p. 208°-210°, $v_{max}$. (CHCl$_3$) 1600, 1490, 1445, 1410 cm$^{-1}$, δ(CDCl$_3$) 2.54 (3H, s), 6.15 (1H, d, J 9 Hz), 6.59 (1H, d, J 9 Hz), 7.35 (15 H, s) p.p.m. (Found: C, 71.65; H, 5.20; N, 14.41%. C$_{23}$H$_{20}$N$_4$S requires C, 71.9; H, 5.21; N, 14.6%).

(ii) Preparation of Silver (Z)-2-(5-Methyltetrazol-1-yl)ethen-1-yl-thiolate

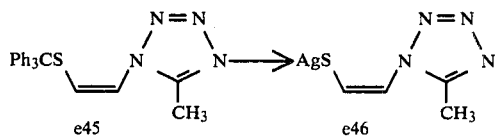

(Z)-1-(5-Methyltetrazol-1-yl)-2-triphenylmethylthioethene, e45, (709 mg) in methanol (100 ml) was heated under reflux until all had dissolved. Pyridine (0.18 ml, 176 mg) in methanol (5 ml) was added followed by silver nitrate (310 mg) in H$_2$O (14 ml) and methanol (7 ml). After heating under reflux for 3 min. the mixture was cooled and stirred at room temperature for 2 hours. The mixture was then centrifuged and the precipitate washed with methanol (2×50 ml) and ether (2×50 ml). After drying in vacuo the silver salt, e46, was obtained as a powder, $v_{max}$. (KBr) 3060, 3020, 2920, 1517, 1385, 1265, 1115, 853, 838, 725, 695 and 665 cm$^{-1}$.

(iii) Preparation of (Z)-2-(5-Methyltetrazol-1-yl)ethen-1-yl Thioacetate

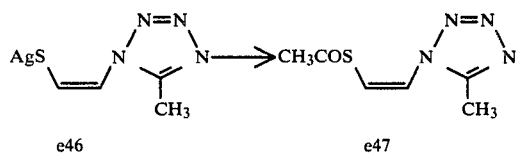

The silver thiolate, e46, (424 mg) in acetonitrile (8 ml) was treated with acetyl chloride (133 mg) in acetonitrile (1.3 ml). After 30 min the solution was diluted with ethyl acetate, filtered through Celite, and the solvents were then evaporated in vacuo. Toluene (20 ml) was added to the residue and evaporated in vacuo (2×). The residue was chromatographed on silica gel (230–400 mesh ASTM) (2.5×15 cm) eluting with ethyl acetate to yield (Z)-2-(5-methyltetrazol-1-yl)ethen-1-yl thioacetate, e47, (65 mg). Crystallisation from ethyl acetate/hexane gave colourless plates m.p. 135°-137°, $v_{max}$. (CH$_2$Cl$_2$) 1715, 1635, 1520, 1410 cm$^{-1}$. δ(CDCl$_3$) 2.51 (3H, s), 2.60 (3H, s), ca 6.9 (1H, d, J 8,5 Hz), ca 7.25 (1H, d J 8.5 Hz) p.p.m.

(iv) Preparation of p-Nitrobenzyl (5RS, 6SR)-3-[(Z)-2-(5-Methyltetrazol-1-yl)ethen-1-yl]thio-6-[(1RS)-p-Nitrobenzyloxycarbonyloxyethyl]-7-oxo-1-azabicyclo[3.2.0]hept-2-ene-2-carboxylate

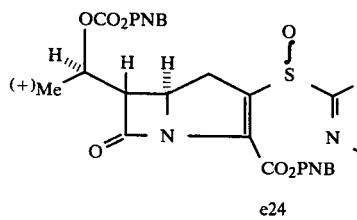

e24

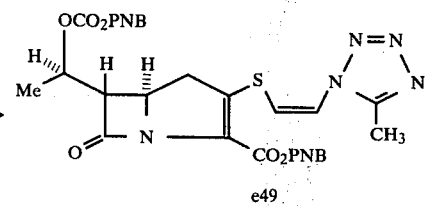

e49

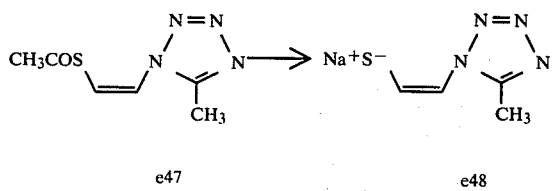

e47    e48

The thioacetate, e47, (50 mg) in dioxan (1 ml) under argon was cooled to 10° and treated with aq. 0.1 N NaOH (5.4 ml). After 15 min. the reaction mixture was allowed to warm to room temperature and left to stand for 15 min. T.l.c. indicated disappearance of starting material and the appearance of a zone on the origin, indicating formation of the sodium thiolate, e48. The volume of the solution was reduced to ca. 3 ml by evaporation in vacuo in order to remove some dioxan. Water (2 ml) was then added to the solution.

The sulphoxide, e24, (164 mg) in dichloromethane (7.5 ml) was treated with benzyldimethyl-n-hexadecylammonium chloride, cooled in an ice bath and then treated with the aqueous solution of the sodium thiolate, e48. After stirring for 30 min. the solution was diluted with dichloromethane (50 ml) and brine (20 ml). The layers were separated and the dichloromethane dried (MgSO$_4$) and evaporated in vacuo. Chromatography of the product on silica gel, eluting with ethyl acetate (300 ml) followed by ethylacetate/ethanol (9:1) gave the product, e49, 100 mg, $\nu_{max}$ (CH$_2$Cl$_2$) 1785, 1750, 1715 (sh), 1605, 1520, 1380, 1350 cm$^{-1}$. $\lambda_{max}$ (EtOH) 333 and 265 nm.

EXAMPLE 23

Preparation of Sodium (5RS, 6RS)-6-[(1RS)-1-Hydroxyethyl]-3-[(Z)-2-(5-methyltetrazol-1-yl)ethenylthio]-7-oxo-1-azabicyclo[3.2.0]hept-2-ene-2-carboxylate

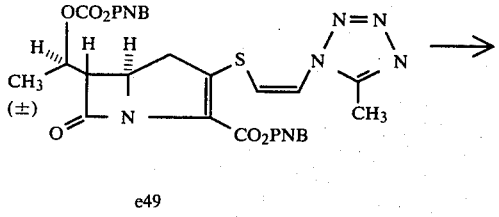

e49

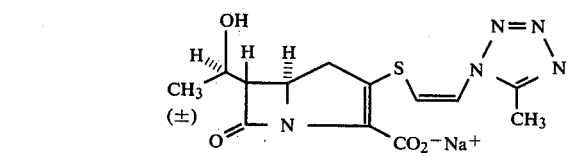

e50

PNB≡CH$_2$—⟨phenyl⟩—NO$_2$

The ester, e49, (100 mg) in dioxan (15 ml) and water (7,5 ml) was hydrogenated over 5% Palladium or carbon catalyst (150 mg) for 2.5 hr. Sodium hydrogen carbonate (13 mg) in water (5 ml) was added and the catalyst was removed by filtration through Celite. The filter cake was washed with water (30 ml) and the volume of combined filtrate and washings were reduced to ca 30 ml. by evaporation in vacuo. The resultant solution was extracted with ethyl acetate (2×50 ml) and the aqueous solution then evaporated in vacuo to ca 10 ml and loaded onto a column of DIAION HP20 (2.5×10 cm). The column was eluted with water (300 ml), water/ethanol (9:1) (200 ml) followed by water/ethanol (8:2) (200 ml). The solution eluted by the aqueous ethanol contained the desired sodium salt, e50. If desired this solution can be evaporated in vacuo to a smaller volume and freeze dried to give the sodium salt (e50) $\lambda_{max}$ (H$_2$O) 313 nm.

| ORGANISM | DEMONSTRATION OF EFFECTIVENESS COMPOUND OF EXAMPLE | | | | |
|---|---|---|---|---|---|
| | 10* | 15* | 17 | 21* | 23 |
| Citrobacter freundii E88 | 6.2 | 0.8 | 3.1 | 0.8 | 0.2 |
| Enterobacter cloacae N1 | 3.1 | 0.8 | NG | 3.1 | 1.6 |
| Escherichia coli O111 | 1.6 | ≦0.1 | 0.8 | 0.4 | 0.4 |
| Escherichia coli JT 39 | 3.1 | 0.2 | 6.2 | 0.8 | 0.1 |
| Klebsiella aerogenes A | 0.8 | 0.2 | 1.6 | 1.6 | 0.2 |
| Proteus mirabilis C977 | 0.8 | 0.8 | 0.8 | 1.6 | 3.1 |
| Proteus morganii I580 | 1.6 | 1.6 | 12.5 | 1.6 | 0.8 |
| Proteus rettgeri WM16 | 3.1 | 1.6 | 3.1 | 3.1 | 1.6 |
| Proteus vulgaris WO91 | 3.1 | 1.6 | 12.5 | 1.6 | 0.8 |
| Pseudomonas aeruginosa A | 100 | 50 | 50 | 25 | 100 |

DEMONSTRATION OF EFFECTIVENESS

| ORGANISM | COMPOUND OF EXAMPLE | | | | |
|---|---|---|---|---|---|
| | 10* | 15* | 17 | 21* | 23 |
| *Salmonella typhimurium* CT10 | 0.8 | 0.8 | 0.8 | 1.6 | 0.4 |
| *Serratia marcescens* US20 | 3.1 | — | — | — | — |
| *Shigella sonnei* MB 11967 | 1.6 | 0.8 | 0.8 | 1.6 | 0.4 |
| *Bacillus subtilis* A | 0.4 | ≦0.1 | ≦0.1 | 0.8 | 0.1 |
| *Staphylococcus aureus* Oxford | 0.8 | 0.2 | ≦0.1 | 0.8 | 0.2 |
| *Staphylococcus aureus* Russell | 1.6 | 0.2 | ≦0.1 | 0.4 | 0.2 |
| *Staphylococcus aureus* 1517 | 50 | 12.5 | 0.8 | 12.5 | 6.2 |
| *Streptococcus faecalis* I | 6.2 | 6.2 | 0.2 | 12.5 | 0.4 |
| *Streptococcus pneumoniae* CN33 | ≦0.1 | ≦0.1 | ≦0.1 | 0.2 | NG |
| *Streptococcus pyogenes* CN10 | 0.2 | ≦0.1 | ≦0.1 | ≦0.1 | NG |
| *E. coli* ESS | 0.4 | ≦0.1 | ≦0.1 | 0.4 | 0.1 |

*Microtitre using Nutrient broth
+ DST agar + 10% horse blood
− inoculum 0.001 ml of a $10^{-2}$ dilution for G + ve bacteria or a $10^{-4}$ dilution for G − ve organisms

What we claim is:
1. A compound of the formula (II):

(II)

a salt thereof or an ester thereof convertible to the free acid or salt thereof by biological or chemical methods wherein $R^3$ is hydrogen or a group of the formula (i):

$$CR^5R^6R^7 \quad (i)$$

wherein $R^5$ is hydrogen, sulphonato-oxy or a salt or ester thereof, hydroxy, alkoxy of 1 to 4 carbon atoms, $OCOR^8$ or $OCO_2R^8$ wherein $R^8$ is alkyl of 1 to 4 carbon atoms, phenyl or benzyl unsubstituted or substituted by fluoro, chloro, bromo, alkoxy of 1 to 3 carbon atoms or nitro; $R^6$ is hydrogen or alkyl of 1 to 4 carbon atoms; and $R^7$ is hydrogen or alkyl of 1 to 4 carbon atoms, n is zero or one, X is a saturated or unsaturated hydrocarbon unsubstituted or substituted by bromo or chloro, and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benozyloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl.

2. A compound according to claim 1 wherein X is alkanediyl of 1 to 6 carbon atoms, alkenediyl of 2 to 6 carbon atoms unsubstituted or substituted by bromo or chloro or cycloalkanediyl of 3 to 8 carbon atoms.

3. A compound of the formula (III):

(III)

or a pharmaceutically acceptable salt or in-vivo hydrolysable ester thereof wherein:
(A) $R^3$ is hydrogen or a group of the sub-formula (a):

$$CR^5R^6R^7 \quad (a)$$

wherein $R^5$ is hydrogen, hydroxy, alkoxy of 1 to 4 carbon atoms, $OCO_2R^8$ wherein $R^8$ is alkyl of 1 to 4 carbon atoms, phenyl, benzyl, fluorobenzyl, chlorobenzyl, bromobenzyl, alkoxybenzyl or nitrobenzyl; $R^6$ is hydrogen or alkyl of 1 to 4 carbon atoms; $R^7$ is hydrogen or alkyl of 1 to 4 carbon atoms; $X^1$ is a group of the sub-formula (b) or (c):

$$-S(O)_n-C_{2-6}- \quad (b)$$

$$-S-CR^9=CR^{10}- \quad (c)$$

wherein n is zero or 1; $R^9$ is hydrogen or alkyl of 1 to 4 carbon atoms; $R^{10}$ is hydrogen or alkyl of 1 to 4 carbon atoms; and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benozyloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl; or (B) $R^3$ is $CH_3CH(OH)O$, $R^4$ is methyl, and $X^1$ is a group of the sub-formula (d) or (e):

$$-S(O)-CH=CH- \quad (d)$$

$$-S-C(Y)=CH- \quad (e)$$

wherein Y is a bromine or chlorine atom;

(C) $R^3$ is $CH_3CH(OSO_3H)-$ or a methyl or ethyl ester thereof; $R^4$ is methyl; and $X^1$ is a group of the sub-formula (f) or (g):

$$-S(O)_n-CH_2-CH_2- \quad (f)$$

$$-S(O)_n-C(Z)=CH- \quad (g)$$

wherein n is zero or 1; and Z is a hydrogen, chlorine or bromine atom; or (D) $R^3$ is $CH_3CH(OSO_3H)-$ or a methyl or ethyl ester thereof; $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benozyloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl; and $X^1$ is —S—CH$_2$—CH$_2$—; or (E) $R^3$ is CH$_3$CH(OSO)$_3$H— or a methyl or ethyl ester thereof; $R^4$ is ethyl; and $X^1$ is —S—CH=CH—; or (F) $R^3$ is CH$_3$CH(SR$^o$)— wherein R$^o$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benozyloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl; $R^4$ is methyl; and $X^1$ is —S—CH$_2$CH$_2$— or a group of the sub-formula (h):

—S(O)$_n$—CH=CH—  (h)

wherein n is zero or 1: with the proviso that when $R^3$ is CH$_3$CH(OSO$_3$H)— or a methyl or ethyl ester thereof, the C-5 and C-6 protons are cis.

4. A compound according to claim 1 wherein the group —S(O)$_n$—X— is —SCH$_2$CH$_2$—.

5. A compound according to claim 1 wherein the group —S(O)$_n$—X— is —SCH=CH—.

6. A compound according to claim 1 wherein $R^4$ is methyl.

7. A compound according to claim 1 of the formula (IV), (V), (VI) or (VII):

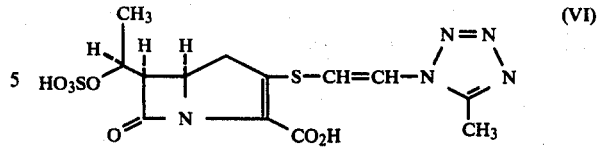

(IV)

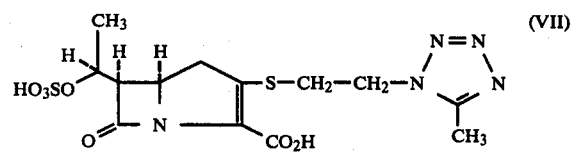

(V)

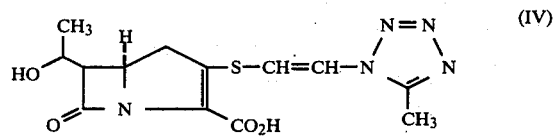

(VI)

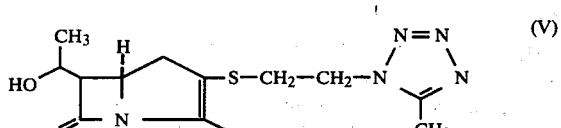

(VII)

or a pharmaceutically acceptable salt or in-vivo hydrolysable ester thereof.

8. A compound according to claim 7 wherein the methyl substituent on the tetrazolyl is replaced by an aminomethyl substituent.

9. A compound according to claim 1 in the form of an alkali metal salt.

10. A compound according to claim 1 selected from:
(5R, 6R)-6-[(1S)-1-Hydroxyethyl]-3-[2-(5-methyltetrazol-1-yl)ethylthio]-7-oxo-1-azabicyclo[3.2.0-]hept-2-ene-2-carboxylic acid, Mono Sodium Salt of (5R, 6R)-6-[(1S)-1-Hydroxysulphonyloxyethyl]-3-[2-(5-methyltetrazol-1-yl)ethylthio]-7-oxo-1-azabicyclo[3.2.0]hept-2-ene-2-, carboxylic acid, (5R, 6S)-3-[2-(5-Methyltetrazol-1-yl)ethylthio]-6-[(1S)-1-hydroxyethyl]-7-oxo-1-azabicyclo[3.2.0.-]hept-2-ene-2-carboxylic acid, Sodium (5R, 6R)-3-[(E)2-(5-Methyltetrazol-1-yl)ethenylthio]-6-[sodium(1S)-1-sulphonatooxyethyl]-7-oxo-1-azabicyclo[3.2.0]hept-2-ene-2-carboxylate, Sodium (5R, 6R)-3-[2-(5-Methyltetrazol-1-yl)ethylthio]-6-[sodium(1S)-1-sulphonatooxyethyl]-7-oxo-1-azabicyclo[3.2.0]hept-2-ene-2-carboxylate, Sodium (5R, 6R)-6-[(1S)-1-Hydroxyethyl]-3-[2-(5-methyltetrazol-1-yl)ethylthio]-7-oxo-1-azabicyclo[3.2.0-]hept-2-ene-2-carboxylate, sodium (5RS, 6SR)-6-[(1RS)-1-Hydroxyethyl]-1-[2-(5-methyltetrazol-1-yl)ethylthio]-7-oxo-1-azabicyclo[3.2.0]hept-2-ene-2-carboxylate, Sodium (5R, 6R)-6-[(1S)-1-Hydroxyethyl]-3-[(E)-2-(5-methyltetrazol-1-yl)ethenylthio]-7-oxo-1-azabicyclo[3.2.0]hept-2-ene-2-carboxylate, Phthalidyl (5R, 6R)-6-[(1S)-1-Hydroxyethyl]-3-[2-(5-methyltetrazol-1-yl)ethyl thio]-7-oxo-1-azabicyclo[3.2.0]hept-2-ene-2-carboxylate and (5RS, 6SR)-3-[2-(5-aminomethyl tetrazol-1-yl)ethylthio]-6-[1(RS)-1-hydroxyethyl thio]-7-oxo-1-azabicyclo[3.2.0]hept-2-ene-2-carboxylate and sodium (5RS, 6RS)-6-[(1RS-1-hydroxyethyl]-3-[(Z)-2-(5-methyltetrazol-1-yl)ethenylthio]-7-oxo-1-azabicyclo[3.2.0]hept-2-ene-2-carboxylate.

11. A compound according to claim 1 wherein $R^3$ is hydroxyethyl and n is zero.

12. A pharmaceutical composition useful for treating bacterial infections in humans and animals which comprises an antibacterially effective amount of a compound of the formula (II):

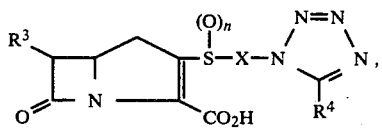

a pharmaceutically acceptable salt thereof or a pharmaceutically acceptable ester thereof convertible to the free acid or salt thereof by biological or chemical methods wherein $R^3$ is hydrogen or a group of the formula (i):

$$CR^5R^6R^7 \qquad (i)$$

wherein $R^5$ is hydrogen, sulphonato-oxy or a salt or ester thereof, hydroxy, alkoxy of 1 to 4 carbon atoms, $OCOR^8$ or $OCO_2R^8$ wherein $R^8$ is alkyl of 1 to 4 carbon atoms, phenyl or benzyl unsubstituted or substituted by fluoro, chloro, bromo, alkoxy of 1 to 3 carbon atoms or nitro; $R^6$ is hydrogen or alkyl of 1 to 4 carbon atoms; and $R^7$ is hydrogen or alkyl of 1 to 4 carbon atoms, n is zero or one, X is a a saturated or unsaturated hydrocarbon unsubstituted or substituted by bromo or chloro, and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl, in combination with a pharmaceutically acceptable carrier.

13. A composition according to claim 12 wherein X is alkanediyl of 1 to 6 carbon atoms, alkenediyl of 2 to 6 carbon atoms unsubstituted or substituted by bromo, chloro or cycloalkanediyl of 3 to 8 carbon atoms.

14. A composition according to claim 12 wherein the group $—S(O)_n—X—$ is $—SCH_2CH_2—$.

15. A composition according to claim 12 wherein the group $—S(O)_n—X—$ is $—SCH=CH—$.

16. A composition according to claim 12 wherein $R^4$ is methyl.

17. A composition according to claim 12 of the formula (IV), (V), (VI) or (VII):

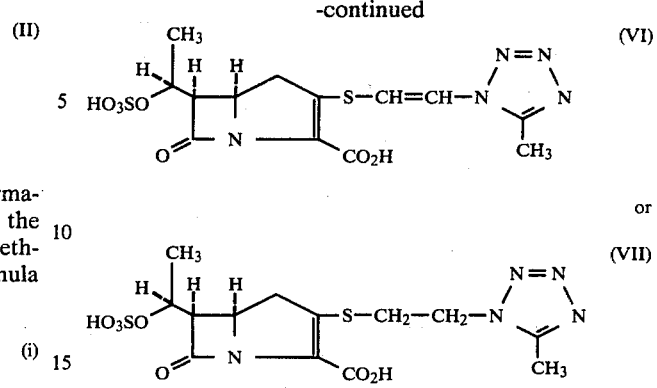

or a pharmaceutically acceptable salt or in-vivo hydrolysable ester thereof.

18. A composition according to claim 17 wherein the methyl substituent on the tetrazolyl is replaced by an aminomethyl substituent.

19. A composition according to claim 12 in the form of an alkali metal salt.

20. A composition according to claim 12 wherein the compound is:

(5R, 6R)-6-[(1S)-1-Hydroxyethyl]-3-[2-(5-methyltetrazol-1-yl)ethylthio]-7-oxo-1-azabicyclo[3.2.0-]hept-2-ene-2-carboxylic acid, Mono Sodium Salt of (5R, 6R)-6-[(1S)-1-Hydroxysulphonyloxyethyl]-3-[2-(5-methyltetrazol-1-yl)ethylthio]-7-oxo-1-azabicyclo[3.2.0]hept-2-ene-2-, carboxylic acid, (5R, 6S)-3-[2-(5-Methyltetrazol-1-yl)ethylthio]-6-[(1S)-1-hydroxyethyl]-7-oxo-1-azabicyclo[3.2.0.-]hept-2-ene-2-carboxylic acid, Sodium (5R, 6R)-3-[(E)2-(5-Methyltetrazol-1-yl)ethenylthio]-6-[sodium(1S)-1-sulphonatooxyethyl]-7-oxo-1-azabicyclo[3.2.0]hept-2-ene-2-carboxylate, Sodium (5R, 6R)-3-[2-(5-Methyltetrazol-1-yl)ethylthio]-6-[sodium(1S)-1-sulphonatooxyethyl]-7-oxo-1-azabicyclo[3.2.0]hept-2-ene-2-carboxylate, Sodium (5R, 6R)-6-[(1S)-1-Hydroxyethyl]-3-[2-(5-methyltetrazol-1-yl)ethylthio]-7-oxo-1-azabicyclo[3.2.0-]hept-2-ene-2-carboxylate, sodium (5RS, 6SR)-6-[(1RS)-1-Hydroxyethyl]-1-[2-(5-methyltetrazol-1-yl)ethylthio]-7-oxo-1-azabicyclo[3.2.0]hept-2-ene-2-carboxylate, Sodium (5R, 6R)-6-[(1S)-1-Hydroxyethyl]-3-[(E)-2-(5-methyltetrazol-1-yl)ethenylthio]-7-oxo-1-azabicyclo[3.2.0]hept-2-ene-2-carboxylate, Phthalidyl (5R, 6R)-6-[(1S)-1-Hydroxyethyl]-3-[2-(5-methyltetrazol-1-yl)ethyl thio]-7-oxo-1-azabicyclo[3.2.0]hept-2-ene-2-carboxylate or (5RS, 6SR)-3-[2-(5-aminomethyl tetrazol-1-yl)ethylthio]-6-[1(RS)-1-hydroxyethyl thio]-7-oxo-1-azabicyclo[3.2.0]hept-2-ene-2-carboxylate and sodium (5RS, 6RS)-6-[(1RS-1-hydroxyethyl]-3-[(Z)-2-(5-methyltetrazol-1-yl)ethenylthio]-7-oxo-1-azabicyclo[3.2.0]hept-2-ene-2-carboxylate.

21. A composition according to claim 12 wherein $R^3$ is hydroxyethyl and n is zero.

22. A pharmaceutical composition useful for treating bacterial infections in humans and animals which comprises an antibacterially effective amount of a compound of the formula (III):

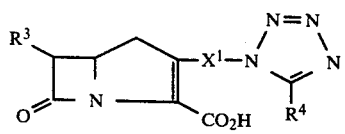

or a pharmaceutically acceptable salt or in-vivo hydrolysable ester thereof wherein:

(A) $R^3$ is hydrogen or a group of the sub-formula (a):

$$CR^5R^6R^7 \qquad (a)$$

wherein $R^5$ is hydrogen, hydroxy, alkoxy of 1 to 4 carbon atoms, $OCO_2R^8$ wherein $R^8$ is alkyl of 1 to 4 carbon atoms, phenyl, benzyl, fluorobenzyl, chlorobenzyl, bromobenzyl, alkoxybenzyl or nitrobenzyl; $R^6$ is hydrogen or alkyl of 1 to 4 carbon atoms; $R^7$ is hydrogen or alkyl of 1 to 4 carbon atoms; $X^1$ is a group of the sub-formula (b) or (c):

$$-S(O)_n-C_{2-6}- \qquad (b)$$

$$-S-CR^9=CR^{10}- \qquad (c)$$

wherein n is zero or 1; $R^9$ is hydrogen or alkyl of 1 to 4 carbon atoms; $R^{10}$ is hydrogen or alkyl of 1 to 4 carbon atoms; and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(phydroxy)benzyl, α-carboxy(p-hydroxy)benzyl, phenyl, furyl, thienyl, hydroxyphenyl, naphthyl, methoxyphenyl, chlorophenyl or methoxycarbonylphenyl, or (B) $R^3$ is $CH_3CH(OH)O$, $R^4$ is methyl, and $X^1$ is a group of the sub-formula (d) or (e):

$$-S(O)-CH=CH- \qquad (d)$$

$$-S-C(Y)=CH- \qquad (e)$$

wherein Y is a bromine or chlorine atom;

(C) $R^3$ is $CH_3CH(OSO_3H)-$ or a methyl or ethyl ester thereof; $R^4$ is methyl; and $X^1$ is a group of the sub-formula (f) or (g):

(f) $\quad -S(O)_n-CH_2-CH_2-$ (g) $\quad -S(O)_n-C(Z)=CH-$ wherein n is zero or 1; and Z is a hydrogen, chlorine or bromine atom; or (D) $R^3$ is $CH_3CH(OSO_3H)-$ or a methyl or ethyl ester thereof; $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl; and $X^1$ is $-S-CH_2-CH_2-$; or (E) $R^3$ is $CH_3CH(OSO)_3H-$ or a methyl or ethyl ester thereof; $R^4$ is ethyl; and $X^1$ is $-S-CH=CH-$; or (F) $R^3$ is $CH_3CH(SR^o)-$ wherein $R^o$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethylbenzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hyroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl, $R^4$ is methyl; and $X^1$ is $-S-CH_2CH_2-$ or a group of the sub-formula (h):

$$-S(O)_n-CH=CH- \qquad (h)$$

wherein n is zero or 1: with the proviso that when $R^3$ is $CH_3CH(OSO_3H)-$ or a methyl or ethyl ester thereof, the C-5 and C-6 protons are cis, in combination with a pharmaceutically acceptable carrier.

23. A method of treating bacterial infections in humans and animals which comprises administering to a human or animal in need thereof an antibacterially effective amount of a compound of the formula (II):

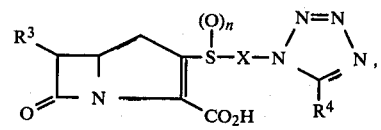

a pharmaceutically acceptable salt thereof or a pharmaceutically acceptable ester thereof convertible to the free acid or salt thereof by biological or chemical methods wherein $R^3$ is hydrogen or a group of the formula (i):

$$CR^5R^6R^7 \qquad (i)$$

wherein $R^5$ is hydrogen, sulphonato-oxy or a salt or ester thereof, hydroxy, alkoxy of 1 to 4 carbon atoms, $OCOR^8$ or $OCO_2R^8$ wherein $R^8$ is alkyl of 1 to 4 carbon atoms, phenyl or benzyl unsubstituted or substituted by fluoro, chloro, bromo, alkoxy of 1 to 3 carbon atoms or nitro; $R^6$ is hydrogen or alkyl of 1 to 4 carbon atoms; and $R^7$ is hydrogen or alkyl of 1 to 4 carbon atoms n is zero or one, X is a a saturated or unsaturated hydrocarbon unsubstituted or substituted by bromo or chloro, and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy(p-hydroxy)benzyl, phenyl, furyl, thienyl, hydroxyphenyl, naphthyl, methoxyphenyl, chlorophenyl or methoxycarbonylphenyl, in combination with a pharmaceutically acceptable carrier.

24. A method according to claim 23 wherein X is alkanediyl of 1 to 6 carbon atoms, alkenediyl of 2 to 6 carbon atoms unsubstituted or substituted by bromo, chloro or cycloalkanediyl of 3 to 8 carbon atoms.

25. A method according to claim 23 wherein the group $—S(O)_n—X—$ is $—SCH_2CH_2—$.

26. A method according to claim 23 wherein the group $—S(O)_n—X—$ is $—SCH=CH—$.

27. A method according to claim 23 wherein $R^4$ is methyl.

28. A method according to claim 23 of the formula (IV), (V), (VI) or (VII):

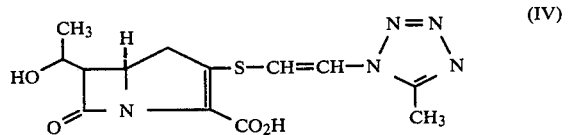

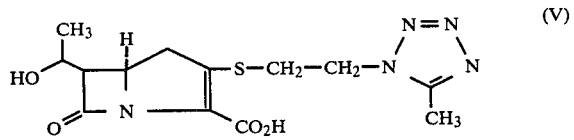

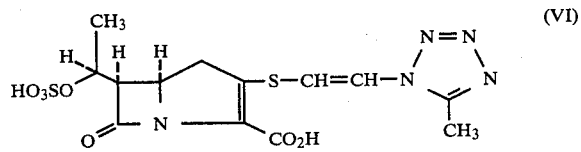

or

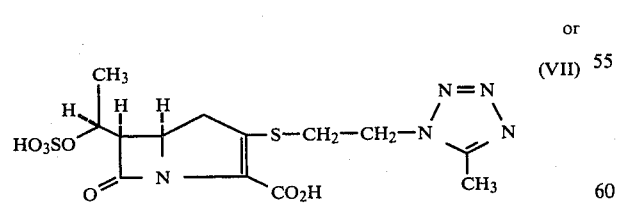

or a pharmaceutically acceptable salt or in-vivo hydrolysable ester thereof.

29. A method according to claim 28 wherein the methyl substituent on the tetrazolyl is replaced by an aminomethyl substituent.

30. A method according to claim 23 in the form of an alkali metal salt.

31. A method according to claim 23 wherein the compound is:

(5R, 6R)-6-[(1S)-1-Hydroxyethyl]-3-[2-(5-methyltetrazol-1-yl)ethylthio]-7-oxo-1-azabicyclo[3.2.0]hept-2-ene-2-carboxylic acid, Mono Sodium Salt of (5R, 6R)-6-[(1S)-1-Hydroxysulphonyloxyethyl]-3-[2-(5-methyltetrazol-1-yl)ethylthio]-7-oxo-1-azabicyclo[3.2.0]hept-2-ene-2-,carboxylic acid, (5R, 6S)-3-[2-(5-Methyltetrazol-1-yl)ethylthio]-6-[(1S)-1-hydroxyethyl]-7-oxo-1-azabicyclo[3.2.0.]hept-2-ene-2-carboxylic acid, Sodium (5R, 6R)-3-[(E)2-(5-Methyltetrazol-1-yl)ethenylthio]-6-[sodium(1S)-1-sulphonatooxyethyl]-7-oxo-1-azabicyclo[3.2.0]hept-2-ene-2-carboxylate, Sodium (5R, 6R)-3-[2-(5-Methyltetrazol-1-yl)ethylthio]-6-[sodium(1S)-1-sulphonatooxyethyl]-7-oxo-1-azabicyclo[3.2.0]hept-2-ene-2-carboxylate, Sodium (5R, 6R)-6-[(1S)-1-Hydroxyethyl]-3-[2-(5-methyltetrazol-1-yl)ethylthio]-7-oxo-1-azabicyclo[3.2.0]hept-2-ene-2-carboxylate, sodium (5RS, 6SR)-6-[(1RS)-1-Hydroxyethyl]-1-[2-(5-methyltetrazol-1-yl)ethylthio]-7-oxo-1-azabicyclo[3.2.0]hept-2-ene-2-carboxylate, Sodium (5R, 6R)-6-[(1S)-1-Hydroxyethyl]-3-[(E)-2-(5-methyltetrazol-1-yl)ethenylthio]-7-oxo-1-azabicyclo[3.2.0]hept-2-ene-2-carboxylate, Phthalidyl (5R, 6R)-6-[(1S)-1-Hydroxyethyl]-3-[2-(5-methyltetrazol-1-yl)ethyl thio]-7-oxo-1-azabicyclo[3.2.0]hept-2-ene-2-carboxylate or (5RS, 6SR)-3-[2-(5-aminomethyl tetrazol-1-yl)ethylthio]-6-[1(RS)-1-hydroxyethyl thio]-7-oxo-1-azabicyclo[3.2.0]hept-2-ene-2-carboxylate and sodium (5RS, 6RS)-6-[(1RS-1-hydroxyethyl]-3-[(Z)-2-(5-methyltetrazol-1-yl)ethenylthio]-7-oxo-1-azabicyclo[3.2.0]hept-2-ene-2-carboxylate.

32. A method according to claim 23 wherein $R^3$ is hydroxyethyl and n is zero.

33. A method of treating bacterial infections in humans and animals which comprises administering to a human or animal in need thereof, an antibacterially effective amount of a compound of the formula (III):

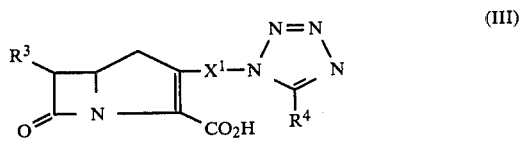

or a pharmaceutically acceptable salt or in-vivo hydrolysable ester thereof wherein:

(A) $R^3$ is hydrogen or a group of the sub-formula (a):

$CR^5R^6R^7$  (a)

wherein $R^5$ is hydrogen, hydroxy, alkoxy of 1 to 4 carbon atoms, $OCO_2R^8$ wherein $R^8$ is alkyl of 1 to 4 carbon atoms, phenyl, benzyl, fluorobenzyl, chlorobenzyl, bromobenzyl, alkoxybenzyl or nitrobenzyl; $R^6$ is hydrogen or alkyl of 1 to 4 carbon atoms; $R^7$ is hydrogen or alkyl of 1 to 4 carbon atoms; $X^1$ is a group of the sub-formula (b) or (c):

wherein n is zero or 1; $R^9$ is hydrogen or alkyl of 1 to 4 carbon atoms; $R^{10}$ is hydrogen or alkyl of 1 to 4 carbon atoms; and $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy (p-hydroxy)benzyl, phenyl, furyl, thienyl, hydroxyphenyl, naphthyl, methoxyphenyl, chlorophenyl or methoxycarbonylphenyl, or (B) $R^3$ is $CH_3CH(OH)O$, $R^4$ is methyl, and $X^1$ is a group of the sub-formula (d) or (e):

$$-S(O)-CH=CH- \quad (d)$$

$$-S-C(Y)=CH- \quad (e)$$

wherein Y is a bromine or chlorine atom;

(C) $R^3$ is $CH_3CH(OSO_3H)$— or a methyl or ethyl ester thereof; $R^4$ is methyl; and $X^1$ is a group of the sub-formula (f) or (g):

$$-S(O)_n-CH_2-CH_2- \quad (f)$$

$$-S(O)_n-C(Z)=CH- \quad (g)$$

wherein n is zero or 1; and Z is a hyrogen, chlorine or bromine atom; or (D) $R^3$ is $CH_3CH(OSO_3H)$—or a methyl or ethyl ester thereof; $R^4$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl, benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hydroxy)benzyl, α-carboxy (p-hydroxy)benzyl, phenyl, furyl, thienyl, hydroxyphenyl, naphthyl, methoxyphenyl, chlorophenyl or methoxycarbonylphenyl; and $X^1$ is $-S-CH_2-CH_2-$; or (E) $R^3$ is $CH_3CH(OSO)_3H$— or a methyl or ethyl ester thereof; $R^4$ is ethyl; and $X^1$ is $-S-CH=CH-$; or (F) $R^3$ is $CH_3CH(SR^o)$— wherein $R^o$ is alkyl of 1 to 6 carbon atoms, alkenyl of 2 to 6 carbon atoms, cyclobutyl, cyclohexyl, hydroxymethyl, hydroxyethyl, hydroxypropyl, methoxymethyl, methoxyethyl, ethoxymethyl, ethoxyethyl, phenoxymethyl, phenoxyethyl, hydroxyphenoxymethyl, aminomethyl, aminoethyl, aminopropyl, phenacylmethyl, benzyloxycarbonylmethyl benzoloxycarbonylethyl, methoxycarbonylmethyl, methoxycarbonylethyl, fluoromethyl, fluoroethyl, cyclopentenyl, cyclohexenyl, benzyl, phenethyl, thienylmethyl, furylmethyl, α-hydroxybenzyl, α-carbonylbenzyl, α-azidobenzyl, α-tetrazolylbenzyl, α-aminobenzyl, p-hydroxybenzyl, α-amino(p-hyroxy)benzyl, α-carboxy (p-hydroxy)benzyl, phenyl, furyl, thienyl, hydroxyphenyl, naphthyl, methoxyphenyl, chlorophenyl or methoxycarbonylphenyl, $R^4$ is methyl; and $X^1$ is $-S-CH_2CH_2-$ or a group of the sub-formula (h):

$$-S(O)_n-CH=CH- \quad (h)$$

wherein n is zero or 1: with the proviso that when $R^3$ is $CH_3CH(OSO_3H)$— or a methyl or ethyl ester thereof, the C-5 and C-6 protons are cis, in combination with a pharmaceutically acceptable carrier.

* * * * *